US011020244B2

(12) United States Patent
Bays et al.

(10) Patent No.: US 11,020,244 B2
(45) Date of Patent: Jun. 1, 2021

(54) BONE HARVESTER AND BONE MARROW REMOVAL SYSTEM AND METHOD

(71) Applicant: Treace Medical Concepts, Inc., Ponte Vedra, FL (US)

(72) Inventors: F. Barry Bays, Collierville, TN (US); David L. Brumfield, Collierville, TN (US); Joe William Ferguson, Ponte Vedra Beach, FL (US); Carlos Eduardo Gil, Jacksonville, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 394 days.

(21) Appl. No.: 15/894,686

(22) Filed: Feb. 12, 2018

(65) Prior Publication Data

US 2018/0161177 A1 Jun. 14, 2018

Related U.S. Application Data

(62) Division of application No. 14/724,072, filed on May 28, 2015, now Pat. No. 9,925,068.

(Continued)

(51) Int. Cl.
*A61F 2/46* (2006.01)
*A61B 17/3205* (2006.01)
*A61B 17/34* (2006.01)
*A61M 5/34* (2006.01)
*A61B 10/02* (2006.01)

(Continued)

(52) U.S. Cl.
CPC .......... *A61F 2/4644* (2013.01); *A61B 10/025* (2013.01); *A61B 17/32053* (2013.01); *A61B 17/3472* (2013.01); *A61M 5/34* (2013.01);

*A61M 5/343* (2013.01); *A61B 10/0283* (2013.01); *A61B 2010/0258* (2013.01); *A61B 2017/0042* (2013.01); *A61B 2017/00455* (2013.01); *A61B 2017/00477* (2013.01); *A61B 2017/320064* (2013.01); *A61B 2090/0807* (2016.02); *A61F 2002/4649* (2013.01)

(58) Field of Classification Search
CPC ............ A61B 10/025; A61B 17/32053; A61B 17/3472; A61B 2090/0807; A61B 10/0283; A61B 2010/0258; A61B 217/0042; A61B 2017/00455; A61B 2017/320064; A61B 2017/00477; A62B 17/1635; A61F 2/4644; A61F 2002/4649; A61M 5/34; A61M 5/343
See application file for complete search history.

(56) References Cited

U.S. PATENT DOCUMENTS 4,543,966 A 10/1985 Islam et al.
5,782,835 A 7/1998 Hart et al.
(Continued)

FOREIGN PATENT DOCUMENTS

CA 2360867 C 8/2008
DE 20010879 U1 10/2000
(Continued)

*Primary Examiner* — Patrick Fernandes
(74) *Attorney, Agent, or Firm* — Fredrikson & Byron, P.A.

(57) ABSTRACT

A bone harvester and bone marrow removal system. The bone harvester can include a body defining a channel extending longitudinally therethrough from a distal to a proximal portion of the body. The distal portion can include a cutting tip. Bone marrow may be drawn through the channel.

15 Claims, 21 Drawing Sheets

Related U.S. Application Data

(60) Provisional application No. 62/005,693, filed on May 30, 2014, provisional application No. 62/040,210, filed on Aug. 21, 2014, provisional application No. 62/051,499, filed on Sep. 17, 2014.

(51) Int. Cl.
  *A61B 17/32* (2006.01)
  *A61B 17/00* (2006.01)
  *A61B 90/00* (2016.01)

(56) References Cited

U.S. PATENT DOCUMENTS

| | | | |
|---|---|---|---|
| 6,022,354 A * | 2/2000 | Mercuri | A61B 17/1635 606/80 |
| 6,080,115 A | 6/2000 | Rubinstein | |
| 6,312,394 B1 | 11/2001 | Fleming, III | |
| 6,416,484 B1 | 7/2002 | Miller et al. | |
| 6,443,910 B1 | 9/2002 | Krueger et al. | |
| 6,450,973 B1 | 9/2002 | Murphy | |
| 6,478,751 B1 | 11/2002 | Krueger et al. | |
| 6,554,778 B1 | 4/2003 | Fleming, III | |
| 6,755,793 B2 | 6/2004 | Lamoureux et al. | |
| 6,783,532 B2 | 8/2004 | Steiner et al. | |
| 6,783,533 B2 | 8/2004 | Green et al. | |
| 6,827,692 B2 | 12/2004 | Castellacci | |
| 6,849,051 B2 | 2/2005 | Sramek et al. | |
| 6,875,183 B2 | 4/2005 | Cervi | |
| 6,875,219 B2 | 4/2005 | Arramon et al. | |
| 6,884,245 B2 | 4/2005 | Spranza, III | |
| 6,890,308 B2 | 5/2005 | Islam | |
| 6,916,292 B2 | 7/2005 | Morawski et al. | |
| 7,014,614 B2 | 3/2006 | Casula | |
| 7,033,324 B2 | 4/2006 | Giusti et al. | |
| 7,077,846 B2 | 7/2006 | Parmigiani | |
| 7,081,123 B2 | 7/2006 | Merboth et al. | |
| 7,115,100 B2 | 10/2006 | McRury et al. | |
| 7,179,232 B2 | 2/2007 | Sutton et al. | |
| 7,201,722 B2 | 4/2007 | Krueger | |
| 7,214,059 B2 | 5/2007 | Takahashi | |
| 7,238,189 B2 | 7/2007 | Schmieding et al. | |
| 7,278,970 B2 | 10/2007 | Goldenberg | |
| 7,278,972 B2 | 10/2007 | Lamoureux et al. | |
| 7,294,132 B2 | 11/2007 | Raskin et al. | |
| 7,331,930 B2 | 2/2008 | Faciszewski | |
| 7,445,624 B2 | 11/2008 | Freier et al. | |
| 7,637,872 B1 | 12/2009 | Fox | |
| 7,637,910 B2 | 12/2009 | Schmieding et al. | |
| 7,662,108 B2 | 2/2010 | Dunker et al. | |
| 7,731,667 B2 | 6/2010 | Goldenberg | |
| 7,819,888 B2 | 10/2010 | Johanson et al. | |
| 7,988,643 B2 | 8/2011 | Hoffmann et al. | |
| 7,993,282 B2 | 8/2011 | Long | |
| 8,016,834 B2 | 9/2011 | Weber et al. | |
| 8,043,291 B2 | 10/2011 | Accordino | |
| 8,070,689 B2 | 12/2011 | Masseglia et al. | |
| 8,070,690 B2 | 12/2011 | Ikehara et al. | |
| 8,088,081 B2 | 1/2012 | Field et al. | |
| 8,177,738 B2 | 5/2012 | Schmieding et al. | |
| 8,182,806 B2 | 5/2012 | Johnson | |
| 8,221,423 B2 | 7/2012 | Gil et al. | |
| 8,241,290 B2 | 8/2012 | Michelson | |
| 8,357,104 B2 | 1/2013 | Moos et al. | |
| 8,439,846 B2 | 5/2013 | Zambelli | |
| 8,523,809 B2 | 9/2013 | Moos et al. | |
| 8,568,334 B2 | 10/2013 | Field et al. | |
| 8,585,610 B2 | 11/2013 | Boock et al. | |
| 8,617,085 B2 | 12/2013 | Moran, Jr. | |
| 8,622,953 B2 | 1/2014 | Hynes et al. | |
| 8,740,811 B2 | 6/2014 | Fortems et al. | |
| 8,777,944 B2 | 7/2014 | Frankhouser et al. | |
| 8,790,349 B2 | 7/2014 | Takahashi | |
| 8,834,417 B2 | 9/2014 | Moos et al. | |
| 8,840,614 B2 | 9/2014 | Mikhail et al. | |
| 8,845,584 B2 | 9/2014 | Ferguson et al. | |
| 8,852,119 B2 | 10/2014 | Ivawrzyniak et al. | |
| 8,858,560 B2 | 10/2014 | Bradley et al. | |
| 2002/0169471 A1 | 11/2002 | Ferdinand | |
| 2003/0236506 A1 | 12/2003 | Schofield et al. | |
| 2004/0073139 A1 | 4/2004 | Hirsch et al. | |
| 2004/0127814 A1 | 7/2004 | Negroni | |
| 2004/0153005 A1 | 8/2004 | Krueger | |
| 2004/0267268 A1 | 12/2004 | Gillespie et al. | |
| 2005/0256425 A1 | 11/2005 | Prusiner | |
| 2005/0267383 A1 | 12/2005 | Groenke et al. | |
| 2006/0058826 A1 | 3/2006 | Evans et al. | |
| 2006/0247552 A1 | 11/2006 | Ikehara et al. | |
| 2006/0276772 A1 | 12/2006 | Moos et al. | |
| 2007/0016100 A1 * | 1/2007 | Miller | A61B 10/0283 600/567 |
| 2007/0055263 A1 | 3/2007 | Way et al. | |
| 2007/0055264 A1 | 3/2007 | Parmigiani | |
| 2007/0055282 A1 | 3/2007 | Muschler | |
| 2007/0060935 A1 | 3/2007 | Schwardt et al. | |
| 2007/0066987 A1 | 3/2007 | Scanlan et al. | |
| 2007/0100286 A1 | 5/2007 | Eltahawy | |
| 2007/0179459 A1 | 8/2007 | Geisler et al. | |
| 2007/0198043 A1 | 8/2007 | Cox et al. | |
| 2007/0208348 A1 | 9/2007 | Parmigiani | |
| 2007/0282220 A1 | 12/2007 | Abemathie | |
| 2007/0293788 A1 | 12/2007 | Entrekin et al. | |
| 2008/0045965 A1 | 2/2008 | Miller et al. | |
| 2008/0058674 A1 | 3/2008 | Jansen et al. | |
| 2008/0119759 A1 | 5/2008 | McLain | |
| 2008/0119821 A1 | 5/2008 | Agnihotri et al. | |
| 2008/0139961 A1 | 6/2008 | Slama et al. | |
| 2008/0214957 A1 | 9/2008 | Verra et al. | |
| 2008/0221527 A1 | 9/2008 | Bradley et al. | |
| 2008/0243163 A1 | 10/2008 | Masseglia et al. | |
| 2008/0262383 A1 | 10/2008 | Routhier et al. | |
| 2009/0149774 A1 | 6/2009 | Simon et al. | |
| 2009/0187116 A1 | 7/2009 | Noishiki et al. | |
| 2009/0209964 A1 | 8/2009 | Yeung | |
| 2009/0216260 A1 | 8/2009 | Souza et al. | |
| 2009/0228012 A1 | 9/2009 | Gangji et al. | |
| 2009/0264888 A1 | 10/2009 | Neumeyer et al. | |
| 2010/0030105 A1 | 2/2010 | Noishiki et al. | |
| 2010/0069786 A1 | 3/2010 | Globerman et al. | |
| 2010/0069788 A1 | 3/2010 | Dell'Oca et al. | |
| 2010/0210967 A1 | 8/2010 | Sjunnesson et al. | |
| 2010/0234761 A1 | 9/2010 | Ramirez et al. | |
| 2011/0071430 A1 | 3/2011 | Chu et al. | |
| 2011/0071535 A1 | 3/2011 | Faccioli et al. | |
| 2011/0082425 A1 | 4/2011 | Wuestemann et al. | |
| 2011/0112436 A1 | 5/2011 | Jones et al. | |
| 2011/0245833 A1 | 10/2011 | Anderson | |
| 2011/0288438 A1 | 11/2011 | Lee | |
| 2012/0022568 A1 | 1/2012 | Koblish et al. | |
| 2012/0041395 A1 | 2/2012 | Sweeney | |
| 2012/0109335 A1 | 5/2012 | May et al. | |
| 2012/0129676 A1 | 5/2012 | Duffy et al. | |
| 2012/0172907 A1 | 7/2012 | Shee et al. | |
| 2012/0323222 A1 | 12/2012 | Kraft et al. | |
| 2012/0330241 A1 | 12/2012 | Haddock et al. | |
| 2013/0012946 A1 | 1/2013 | Janssens | |
| 2013/0123662 A1 | 5/2013 | Hipp | |
| 2013/0123724 A1 | 5/2013 | Allee et al. | |
| 2013/0131545 A1 | 5/2013 | Azimpoor et al. | |
| 2013/0131546 A1 | 5/2013 | Azimpoor et al. | |
| 2013/0150752 A1 | 6/2013 | Swann | |
| 2013/0204160 A1 * | 8/2013 | McKenna | A61B 10/025 600/566 |
| 2014/0031772 A1 | 1/2014 | Hardy et al. | |
| 2014/0127809 A1 | 5/2014 | Kurek et al. | |
| 2014/0148832 A1 | 5/2014 | Walton et al. | |
| 2014/0194880 A1 | 7/2014 | Schmieding et al. | |
| 2014/0257133 A1 | 9/2014 | Landrigan et al. | |
| 2014/0257134 A1 | 9/2014 | Miller et al. | |
| 2014/0257483 A1 | 9/2014 | Swann | |
| 2014/0262408 A1 | 9/2014 | Woodard | |
| 2014/0276205 A1 | 9/2014 | Miller et al. | |
| 2014/0276206 A1 | 9/2014 | Woodward et al. | |

(56) References Cited

U.S. PATENT DOCUMENTS

| | | |
|---|---|---|
| 2014/0277020 A1 | 9/2014 | Koogle et al. |
| 2014/0288499 A1 | 9/2014 | Miller |
| 2014/0288534 A1 | 9/2014 | Howard et al. |

FOREIGN PATENT DOCUMENTS

| | | |
|---|---|---|
| DE | 20109331 U1 | 8/2001 |
| DE | 10042035 A1 | 3/2002 |
| DE | 60101003 T2 | 7/2004 |
| DE | 102009010520 A1 | 9/2010 |
| EP | 1396230 A1 | 3/2004 |
| EP | 1653862 A1 | 5/2006 |
| EP | 1210911 B1 | 1/2011 |
| EP | 2563243 A2 | 3/2013 |
| GB | 2403419 A | 1/2005 |
| IN | 201302410 P4 | 5/2014 |
| JP | 3877982 B2 | 2/2007 |
| JP | 2009034190 A | 2/2009 |
| JP | 4918086 B2 | 4/2012 |
| RU | 2012119245 A | 11/2013 |
| WO | 2004082484 A1 | 9/2004 |
| WO | 2005009246 A1 | 2/2005 |
| WO | 2010046426 A1 | 4/2010 |
| WO | 2010118831 A1 | 10/2010 |
| WO | 2011135070 A2 | 11/2011 |
| WO | 2014022567 A1 | 2/2014 |
| WO | 2014026871 A1 | 2/2014 |
| WO | 2014026875 A1 | 2/2014 |
| WO | 2014070804 A1 | 5/2014 |

\* cited by examiner

BONE HARVESTER AND BONE MARROW REMOVAL SYSTEM AND METHOD

RELATED APPLICATIONS

This application is a divisional application of U.S. patent application Ser. No. 14/724,072, filed May 28, 2015, which claims the benefit of U.S. Provisional Patent Application Ser. Nos. 62/005,693, 62/040,210, and 62/051,499 respectively filed May 30, 2014, Aug. 21, 2014, and Sep. 17, 2014, the entire contents of which are incorporated herein by reference.

TECHNICAL FIELD

This disclosure generally relates to systems and methods for harvesting bone and/or obtaining bone marrow samples.

BACKGROUND

In some instances, material can be placed in apposition to bone to promote healing. For example, various procedures, such as a bone graft, utilize bone and/or bone marrow harvested from a patient to fill a void and/or to facilitate healing. Accordingly, in some instances, it can be beneficial to remove bone and/or bone marrow from an anatomical region to prepare a grafting material.

In an exemplary application, grafting material can be used during a surgical procedure, such as a bone alignment, osteotomy, fusion procedure, fracture repair, and/or other procedures where one or more bones are to be set in a desired position and bone fusion is desired. Such a procedure can be performed, for example, on bones (e.g., adjacent bones separated by a joint or different portions of a single bone) in the foot or hand. In one example, a procedure can be to correct an alignment between a metatarsal (e.g. a first metatarsal) and a cuneiform (e.g., a first/medial cuneiform), such as a bunion correction. An example of such a procedure is a lapidus procedure. In another example, the procedure can be performed by modifying an alignment of a metatarsal (e.g. a first metatarsal). An example of such a procedure is a basilar metatarsal osteotomy procedure.

SUMMARY

In general, this disclosure is directed to systems and methods for harvesting bone and/or obtaining a bone marrow sample. Some embodiments allow for both harvesting of bone and obtaining bone marrow samples at a single location through an outer layer of tissue. Harvested bone can be guided into an internal channel of a bone harvesting device, and the same bone harvesting device may be used to draw bone marrow.

One embodiment includes a bone harvester and bone marrow removal system. The system may include a bone harvester and a bone marrow sample connector. The bone harvester can include a body having a distal portion and a proximal portion, with the body defining a channel extending longitudinally through the body from the distal portion to the proximal portion. The channel and the bone marrow sample connector may be in fluid communication. The proximal portion can be adapted to be rotationally driven, and the distal portion can include a cutting tip. The cutting tip may have a first blade that includes a base on a first end of the first blade disposed at the distal portion of the body, where the base extends along the distal portion of the body defining the channel from a first edge of the base to a second edge of the base. The first blade can also include an apex on a second end of the first blade substantially opposite the first end in a direction spaced from the distal portion of the body, where the apex extends radially inward relative to the distal portion of the body defining the channel over at least a portion of the channel.

Another embodiment includes a method of obtaining bone and bone marrow. The method may include morselizing bone at a first incision by causing a bone harvester to be rotationally driven. The bone harvester can include a body having a distal portion and a proximal portion, and the body may define a channel extending longitudinally through the body from the distal portion to the proximal portion. The method can also include drawing bone marrow at a bone marrow sample connector that is in fluid communication with the channel, where the bone marrow is also drawn at the first incision.

A further embodiment includes a bone harvester that includes a body having a distal portion and a proximal portion, where the body defines a channel extending longitudinally through the body from the distal portion to the proximal portion. The proximal portion may be adapted to be rotationally driven. The bone harvester may also include a stylet having a first portion disposed within the channel and a second portion extending out from the distal portion of the body, with the second portion of the stylet including a pointed tip. A cutting tip can also be included, at the distal portion of the body, where the cutting tip includes a first blade. The first blade can include a base on a first end of the first blade disposed at the distal portion of the body, with the base extending along the distal portion of the body defining the channel from a first edge of the base to a second edge of the base. The first blade can also have an apex on a second end of the first blade substantially opposite the first end in a direction spaced from the distal portion of the body.

An additional embodiment includes a bone harvester and bone marrow removal system. The embodiment of the bone harvester and bone marrow removal system can include a bone harvester and a bone marrow needle disposed partially within the bone harvester. The bone harvester may have a body defining a distal portion and a proximal portion as well as a channel extending longitudinally through the body from the distal portion to the proximal portion. The proximal portion can be adapted to be rotationally driven. The distal portion of the body can have a cutting tip, where the cutting tip includes a first blade. The first blade may have a base on a first end of the first blade disposed at the distal portion of the body, with the base extending along the distal portion of the body defining the channel from a first edge of the base to a second edge of the base. The first blade may also have an apex on a second end of the first blade substantially opposite the first end in a direction spaced from the distal portion of the body. The bone marrow needle may be disposed partially within the channel of the bone harvester. The bone marrow needle can include a body having a proximal end and a distal end, where the body of the bone marrow needle defines a lumen extending longitudinally through the body of the bone marrow needle from the proximal end to the distal end. The bone marrow needle can also have a cutting edge on the distal end of the body of the bone marrow needle, where the cutting edge extends out from the distal portion of the body of the bone harvester.

The details of one or more examples are set forth in the accompanying drawings and the description below. Other features, objects, and advantages will be apparent from the description and drawings, and from the claims.

BRIEF DESCRIPTION OF DRAWINGS

The following drawings are illustrative of particular embodiments of the present invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Some embodiments of the invention include a bone harvester and bone marrow removal system. Such a system is useful for obtaining a sample of bone marrow, such as by aspiration, and harvesting bone during a medical procedure (e.g., a bone grafting or drilling procedure). Some embodiments can allow a practitioner to obtain both bone and bone marrow samples making only one entrance through an outer layer of tissue. Further, in some embodiments, the system allows for precise control and keeps components of the system concentric and aligned to the original and initial penetration hole. Also in some embodiments, the system allows for effective removal of a bone sample from the bone harvester.

Figure 1A:
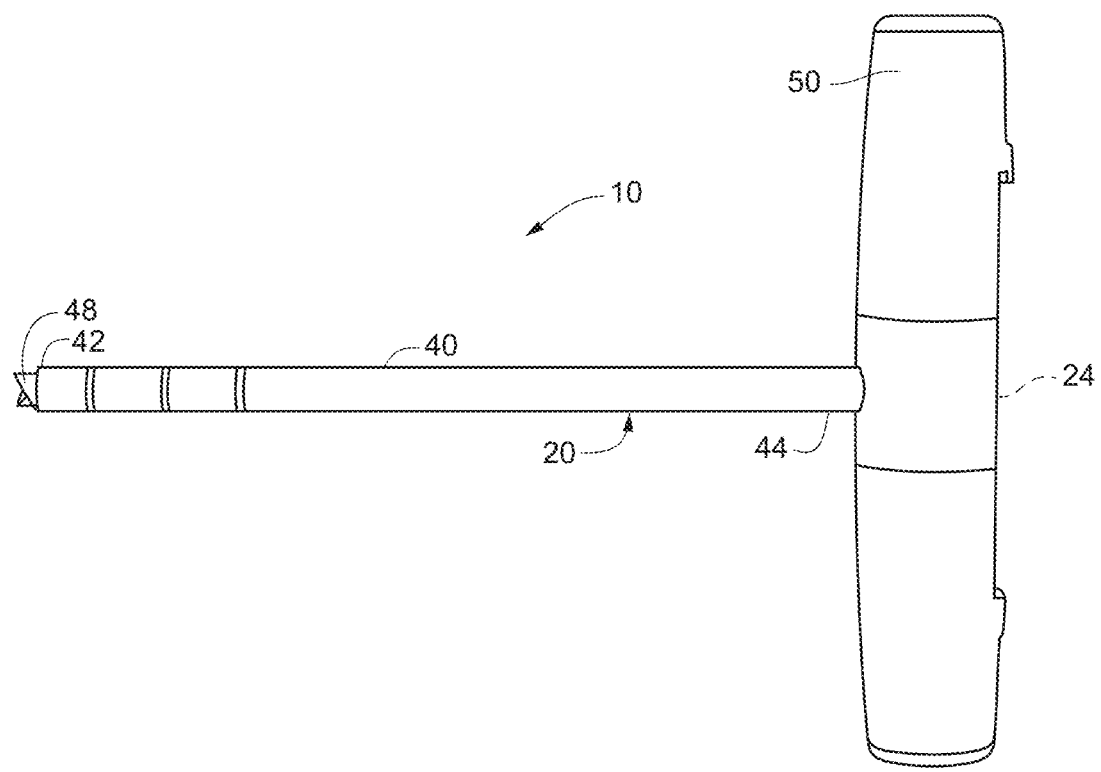
FIG. 1A is a side view of an embodiment of a bone harvester and bone marrow removal system.
Figure 1B:
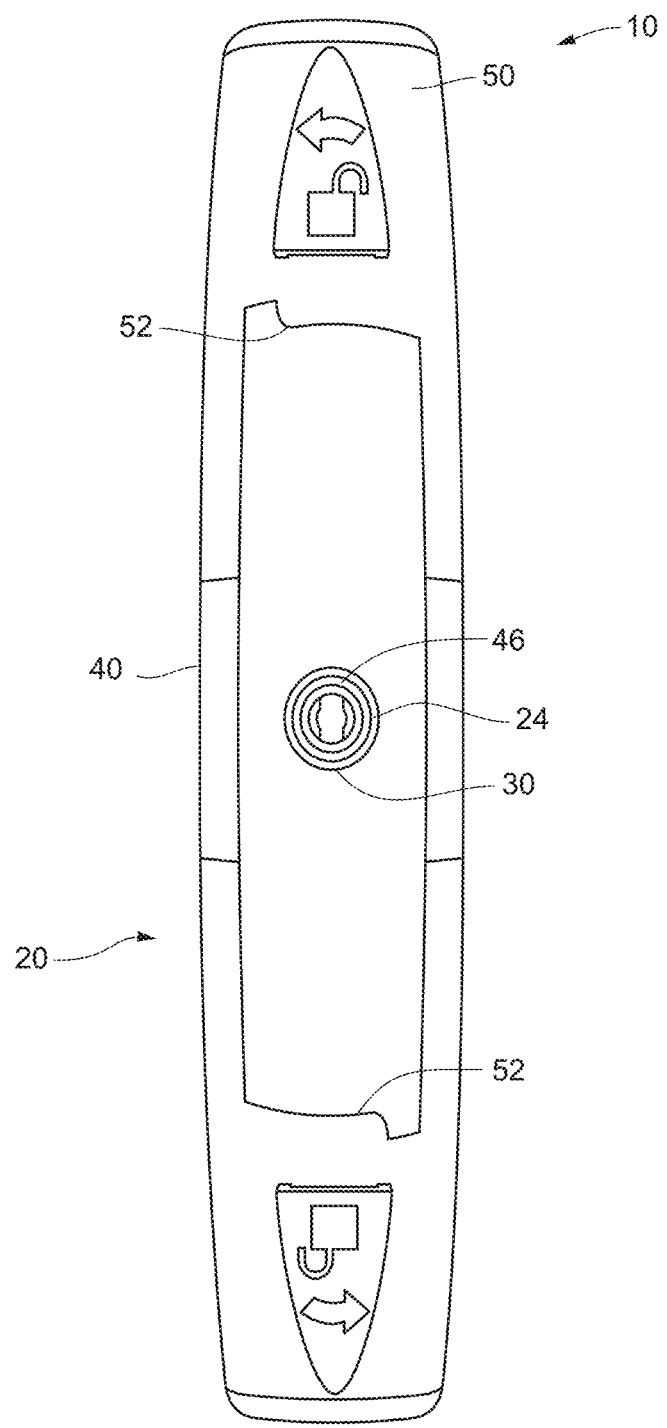
FIG. 1B is top view of a proximal portion of the bone harvester and bone marrow removal system of FIG. 1A.
Figure 1C:
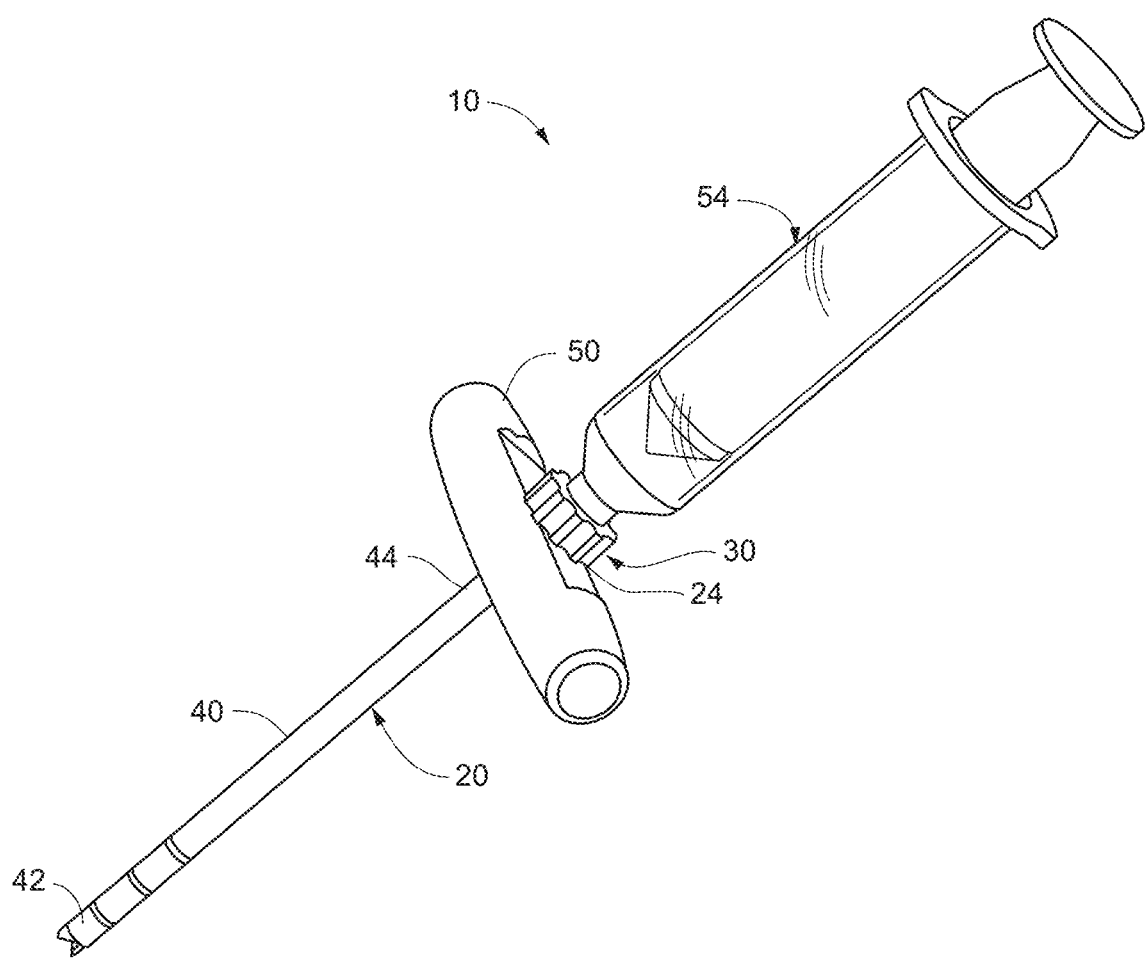
FIG. 1C is a perspective view of the bone harvester and bone marrow removal system of FIG. 1A showing an embodiment where a suction device is coupled to a bone marrow sample connector.

FIGS. 1A-1C show an embodiment of a bone harvester and bone marrow removal system 10. FIG. 1A illustrates a side view of the bone harvester and bone marrow removal system 10, FIG. 1B illustrates a top view of a portion of the bone harvester and bone marrow removal system 10, and FIG. 1C illustrates a perspective view of the bone harvester and bone marrow removal system 10. As shown, the system 10 can include a bone harvester device 20 with a port 24 adapted to receive a component. In the embodiment shown in FIGS. 1B and 1C, the component is a bone marrow sample connector 30.

The bone harvester device 20 includes a body 40 having a distal portion 42 and a proximal portion 44. The distal and proximal portions 42, 44 can be integral or provided as separate joined members as desired. The body 40 of the bone harvester device 20 can define a channel 46 (shown in FIG. 1B) extending longitudinally through at least a portion of an interior of the body 40. In the example shown, the channel 46 extends longitudinally through the body 40 from the distal portion 42 to the proximal portion 44.

The distal portion 42 of the body 40 can include any tip useful for morselizing and/or removing bone. In the illustrated embodiment, the distal portion 42 includes a cutting tip 48, which is shown and described in detail with reference to FIGS. 2A-D. The proximal portion 44 of the body 40 may be adapted to be rotationally driven relative to bone, such as by manual or mechanical power. Such rotation may be oscillating or unidirectional. As illustrated, in some examples the proximal portion 44 can include a driver 50 configured for rotatingly driving the body 40 relative to bone. In examples where manual power is to be used to rotatingly drive the body 40 relative to bone, the driver 50 can be dimensioned to be gripped by a hand of a user (e.g., a handle, as shown). In examples where mechanical power is to be used to rotatingly drive the body 40 relative to bone, the driver 50 at the proximal portion 44 can be adapted to be coupled to a mechanical driving device. In some instances, the driver 50 can be both dimensioned to be gripped by a hand of a user and adapted to be coupled to a mechanical driving device.

The bone harvester device may be configured to receive various components (examples of which will be described herein). Such components may, in some applications, extend through port 24. In some embodiments, the port is aligned with the longitudinal axis of the body and the channel.

In certain embodiments, components can be secured to the body 40 at the driver 50. For instance, the driver 50 as shown includes locking features 52 useful for securing a component to the body 40 at the driver 50. Locking features 52 are shaped so that the component can be rotatingly secured at the driver 50 by rotating the component in a first direction until an interference fit with the locking features 52 prevents further rotation of the component in the first direction. The component may be removed from the body 40 by rotating the component in a second direction, opposite the first direction, and thus away from the interference fit created by the locking features 52. The driver 50 can include, as is shown in FIG. 1B, symbols to indicate the direction of rotation of the component for unlocking the component from the driver 50, and thus the body 40. A component received and secured at the driver 50 is further illustrated and described below with reference to FIGS. 3A-3E.

As noted, the system 10 may include a bone marrow sample connector 30. The bone marrow sample connector 30 can be in fluid communication with the channel 46. Depending on the application of the system 10, the connector 30 may be in fluid communication with the channel 46 at various locations along the body 40 to suit the environment in which the system 10 is desired to be used. In some applications of the system 10, the connector 30 can be disposed at or near the proximal portion 44 of the body 40. In the particular example shown, the connector 30 is disposed at the driver 50 such that the connector 30 is in fluid communication with the channel 46 at the driver 50. Locating the connector 30 at or near the proximal portion 44, and thus opposite the cutting tip 48 at the distal portion 42, may more easily facilitate the coupling of one or more external devices to the connector 30 during operation of the system 10. In some embodiments, the connector is aligned along a longitudinal axis of the body, which allows marrow to be drawn directly through the harvester to the connector. The connector can be engaged with the port 24 or be integrally formed with the bone harvester. For example, the connector 30 can in some embodiments include a threaded connector formed in the driver 50.

The bone marrow sample connector 30 can include any structure useful for connecting an external device to the connector 30, and thus also to the channel 46. As shown in FIG. 1C, the connector 30 can include a Luer-type connector. In one application, an external device may be coupled with the connector 30 to allow for an aspiration procedure as desired, such as drawing a bone marrow sample through the channel 46 from the proximal portion 42 to the external device coupled to the connector 30. In such an application, the external device coupled to the connector 30 may be a suction device 54 useful for applying a vacuum (or suction force) within the channel 46, such as a syringe. FIG. 1C illustrates an example where the suction device 54 is connected to the connector 30 and in fluid communication with the channel 46. In embodiments where the connector is aligned along a longitudinal axis of the body, pressure drops are minimized as the marrow can be drawn directly from the bone into the suction device along a generally linear path.

Figure 2A:
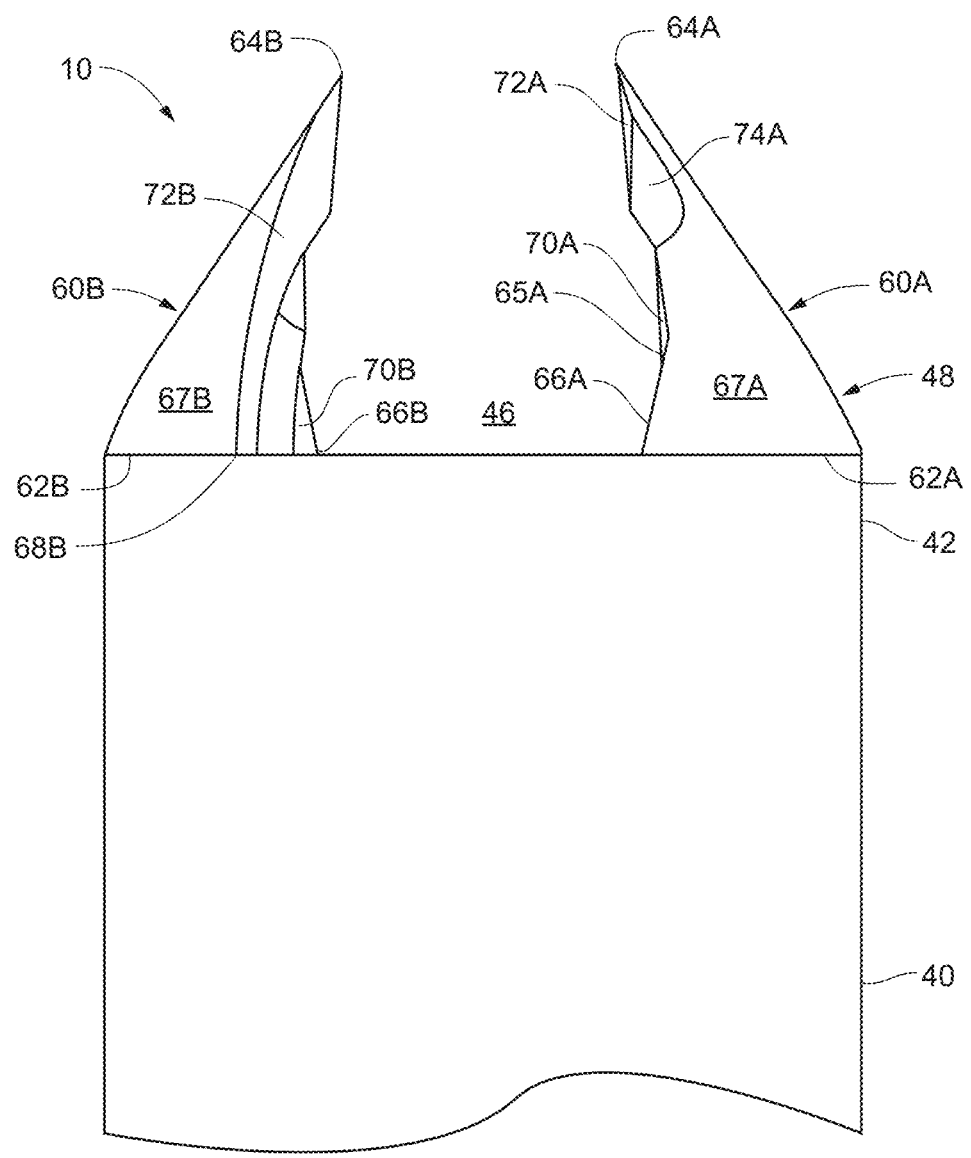
FIG. 2A is a side view of a distal portion of the bone harvester and bone marrow removal system of FIG. 1A showing a cutting tip.
Figure 2B:
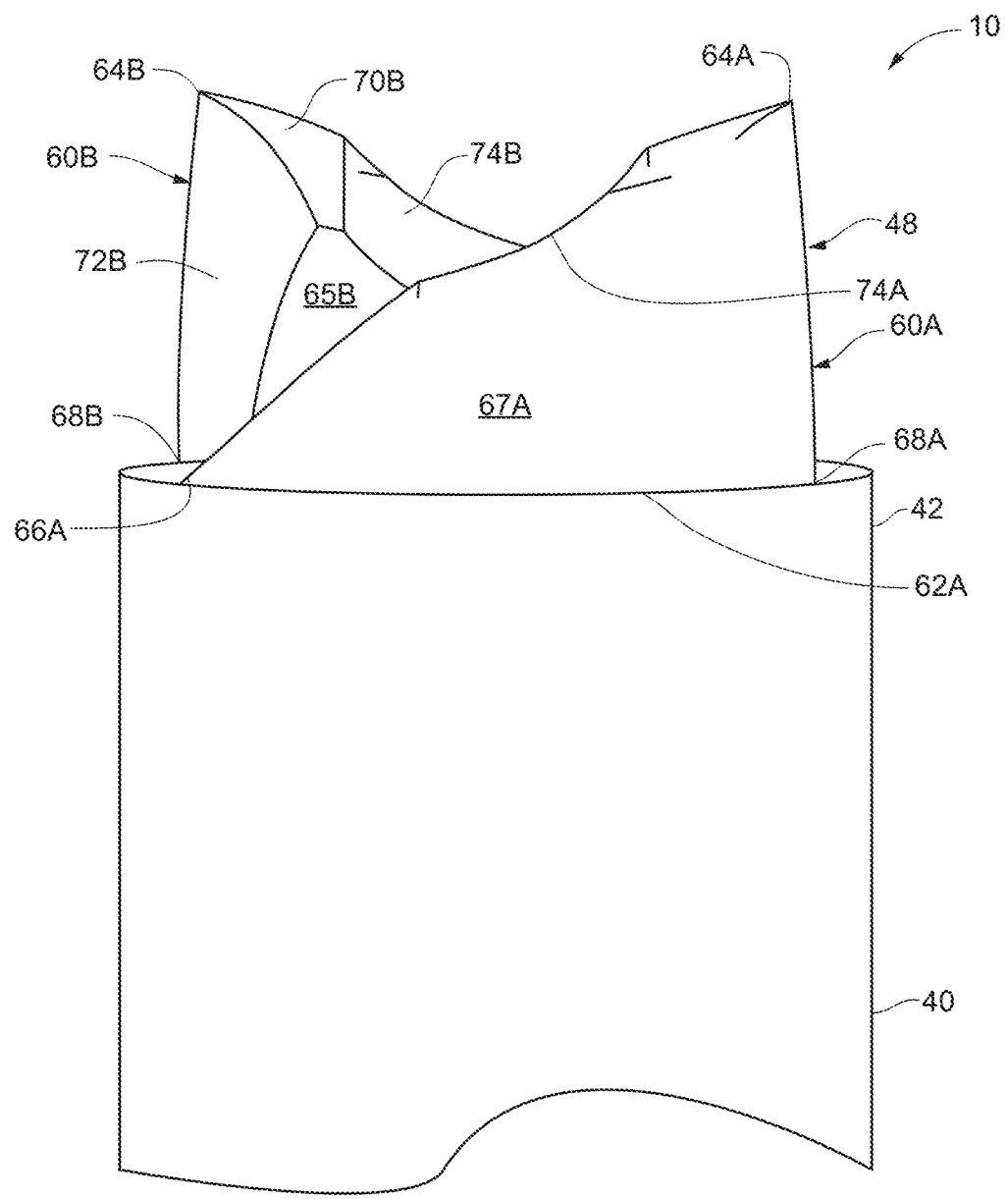
FIG. 2B is a side view, rotated relative to the side view of FIG. 2A, of the distal portion of the bone harvester and bone marrow removal system of FIG. 1A showing the cutting tip.
Figure 2C:
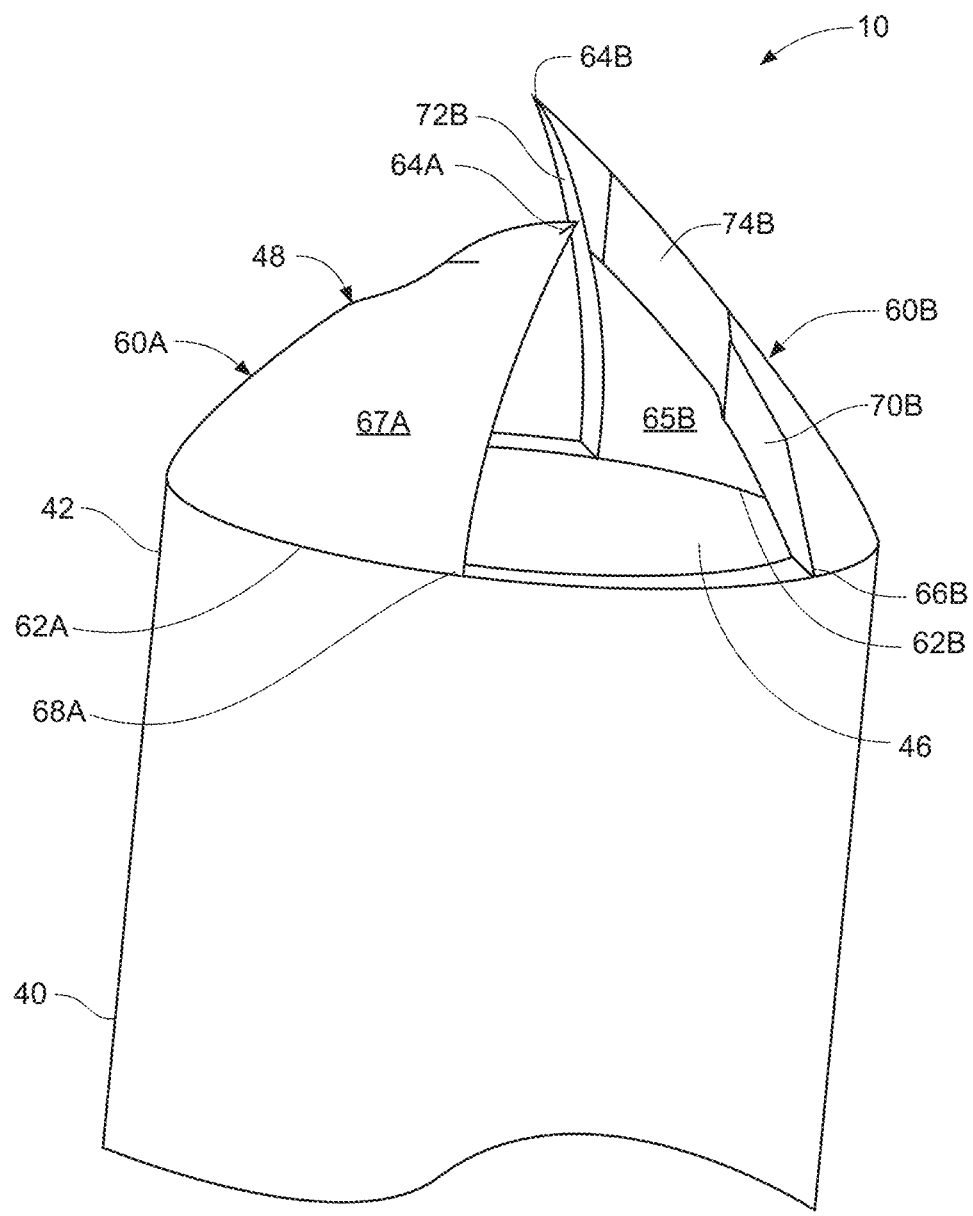
FIG. 2C is a perspective view of the distal portion of the bone harvester and bone marrow removal system of FIG. 1A showing the cutting tip.
Figure 2D:
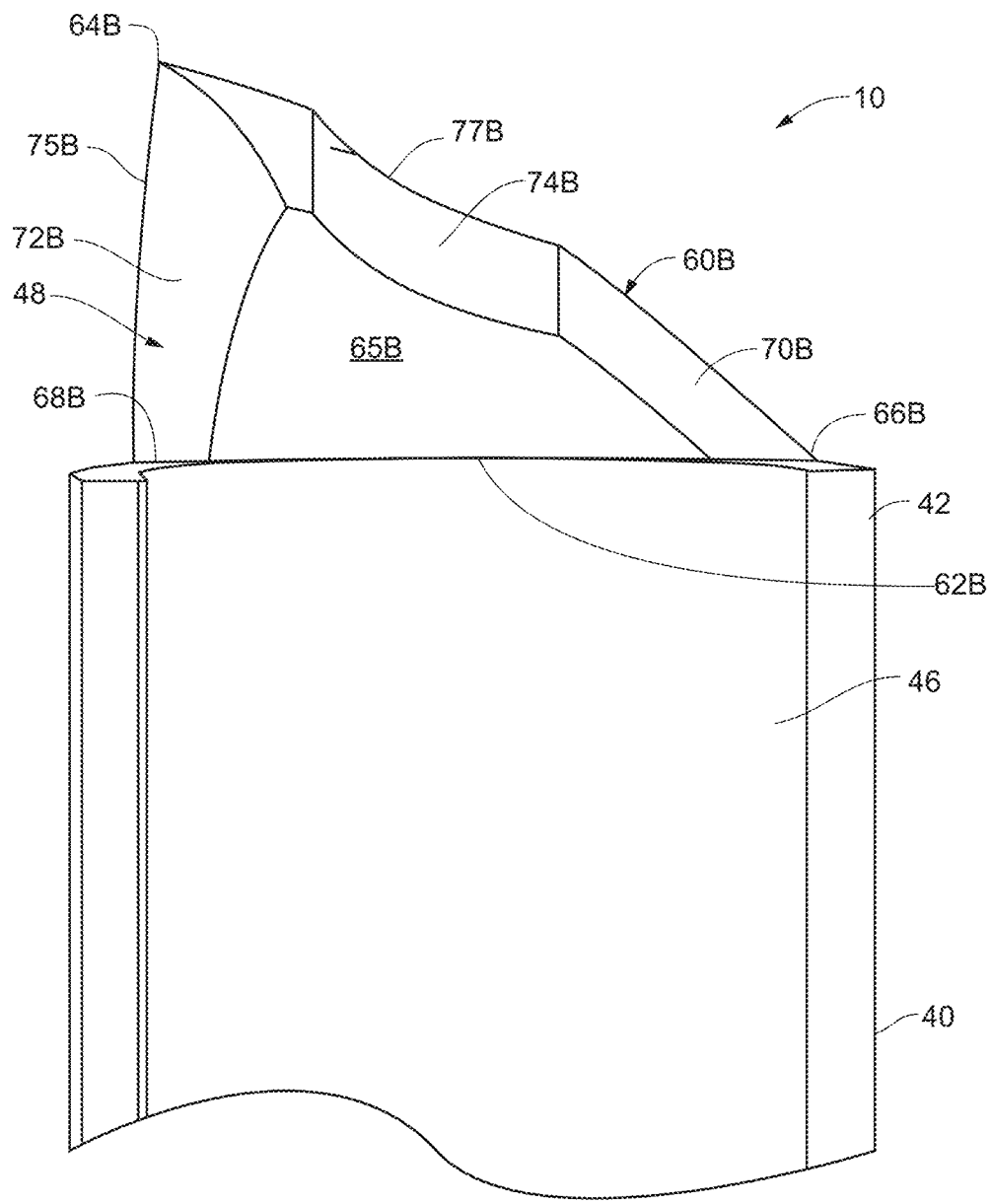
FIG. 2D is a cross-sectional view of a body of a bone harvester showing a blade of the cutting tip.

FIGS. 2A-2D show the cutting tip 48 of the bone harvester and bone marrow removal system 10. FIG. 2A is a side view of the distal portion 42 of the bone harvester and bone marrow removal system 10 showing the cutting tip 48. FIG. 2B is a side view, rotated approximately 90° relative to the side view of FIG. 2A, showing the cutting tip 48. FIG. 2C is a perspective view of the distal portion 42 showing the cutting tip 48. FIG. 2D is a cross-sectional view showing a blade of the cutting tip 48.

As illustrated, the cutting tip 48 is included at the distal portion 42 of the body 40 and may be used for cutting bone. Embodiments of the cutting tip cut bone into particles and guide the particles through the channel and into the interior of the body where it is retained until it is removed for further use. In certain embodiments, the cutting tip can cut bone in both a single direction of rotation and an oscillating motion (e.g., +/−5 degrees to about +/−360 degrees). In the illustrated embodiment, the cutting tip 48 includes a first blade 60A and a second blade 60B, but in other embodiments the cutting tip 48 can include any number of blades as needed for a particular application. Where two blades are included, as is shown, the blades 60A and 60B may be located on substantially opposite sides of the channel 46 from each other and may be mirror images of each other. The one or more blades 60A, 60B may be integral with the distal portion 42 of the body 40, or in other embodiments the one or more blades 60A, 60B may be separately coupled to the distal portion 42.

Each blade 60A, 60B can include a respective base 62A, 62B, a respective apex 64A, 64B, and respective major inner surfaces 65A, 65B and major outer surfaces 67A, 67B. As shown, the major inner surfaces can be generally concave and the major outer surfaces can be generally convex. Each respective base 62A, 62B may be on a first end of each respective blade 60A, 60B, the first end being disposed at the distal portion 42 of the body 40. Each base 62A, 62B can extend along a portion of a perimeter, defining the channel 46, at the end of the distal portion 42 (e.g., a portion of a circumference at the end of the distal portion 42 where the body 40 defines a circular cross section) from a respective first edge 66A, 66B to a respective second edge 68A, 68B. In some embodiments, one or more of such edges can include a radius transition between the blade and the perimeter of the body. As shown, the perimeter of the distal portion 42 can include one or more sections (e.g., two) without blades, such sections extending between bases 62A, 62B. In certain embodiments, such sections may include between about 10 and about 50% of the perimeter of the distal portion.

Each respective apex 64A, 64B may be on a second end of each respective blade 60A, 60B, the second end being substantially opposite the first end in a distal direction spaced from the distal portion 42. In the embodiment shown, extending from each respective first edge 66A, 66B of each base 62A, 62B to a respective apex 64A, 64B is a respective first surface 70A, 70B, which also interfaces with and extends between respective major inner surfaces 65A, 65B and respective major outer surfaces 67A, 67B. In addition, again in the embodiment shown, extending from each respective second edge 68A, 68B of each base 62A, 62B to a respective apex 64A, 64B is a respective second surface 72A, 72B, which also interfaces with and extends between respective major inner surfaces 65A, 65B and respective major outer surfaces 67A, 67B.

In the example shown, each first surface 70A, 70B includes curvature in a direction from the respective first edge 66A, 66B toward the respective second edge 68A, 68B. Each respective apex 64A, 64B can be disposed aft, in a direction along the perimeter defining the channel 46 at the end of the distal portion 42, of each respective first edge 66A, 66B. Also in the example shown, along at least a portion of each second surface 72A, 72B a curvature is included in a direction aft of each respective second edge 68A, 68B. The respective apex 64A, 64B can also be disposed aft of the respective second edge 68A, 68B (shown, for example, in FIG. 2C).

In some embodiments, each respective blade 60A, 60B can extend inwards towards a centerline of the channel in a direction from the respective base 62A, 62B to the respective apex 64A, 64B. In some embodiments, such as the example illustrated, the curvature of the major inner surface 65A, 65B, the curvature along the first surface 70A, 70B, and/or the curvature along the second surface 72A, 72B can be in a direction radially inward relative to the end of the distal portion 42 where the respective bases 62A, 62B are disposed such that the curvature extends in a radial direction over the channel 46. In the embodiment shown, the respective apex 64A, 64B extends radially inward relative to the end of the distal portion 42, where the respective bases 62A, 62B are disposed, defining the channel 46 such that the respective apex 64A, 64B extends over at least a portion of the channel 46 (shown, for example, in FIGS. 2A and 2C). In some embodiment, each apex may extend from the perimeter of the distal portion 42 of the body 40 toward a centerline of the channel 46 at least 25 percent of the diameter of the channel.

The shape of each surface can be useful for morselizing bone and/or guiding morselized bone into the channel. When a surface is provided with a curvature, such curvature may have a relatively constant radius of curvature across the surface or the radius of curvature may vary across the surface. In addition, in some embodiments, the first surface 70A, 70B and/or the second surface 72A, 72B can include a discontinuity along the surface, such as where the surfaces changes from generally flat to concave or convex, from concave to convex, or from convex to concave. For example, as shown, both first surfaces 70A and 70B include a depression section 74A, 74B along a portion of the first surfaces 70A and 70B, such depression being generally concave. In FIG. 2D, lines of demarcation represent the transition between the planes of surfaces 70B and 72B, surface 70B and section 74B, and between surfaces 70B, 72B, section 74B, and surface 65B.

Further, the interface between adjacent surfaces may include an edge as generally depicted in the Figures, or such interface may include a transition region where the surfaces gradually transition between each other. As shown in FIG. 2D, outer edges 75B and 77B can be sharp cutting edges. In the embodiment shown outer edges 75B and 77B are separated by apex 64B and respectively extend from the apex 64B to second edge 68B and first edge 66B. As shown, edge 75B may include a curvature, and edge 77B may include a compound curvature. Although not labeled, such edges can also be provided on blade 60A.

The described configuration of the cutting tip 48 can be useful in applications where the system 10 is to be used for cutting bone. For instance, the system 10 can be placed in a manner to allow the distal portion, and in particular the cutting tip 48, to contact bone at an incision. The system 10 can be rotationally driven in a direction to cut bone. Rotation in this manner along with the described configuration of each blade 60A, 60B may useful for guiding portions of bone being cut (e.g. morselized bone) into the channel 46. The channel 46 can then be used to retain the morselized bone as additional bone continues to be cut at the incision as desired. In some embodiments, morselized bone includes a plurality of non-homogenous bone particles, and can be distinguished from homogenous bone core or plug samples.

Figure 3A:
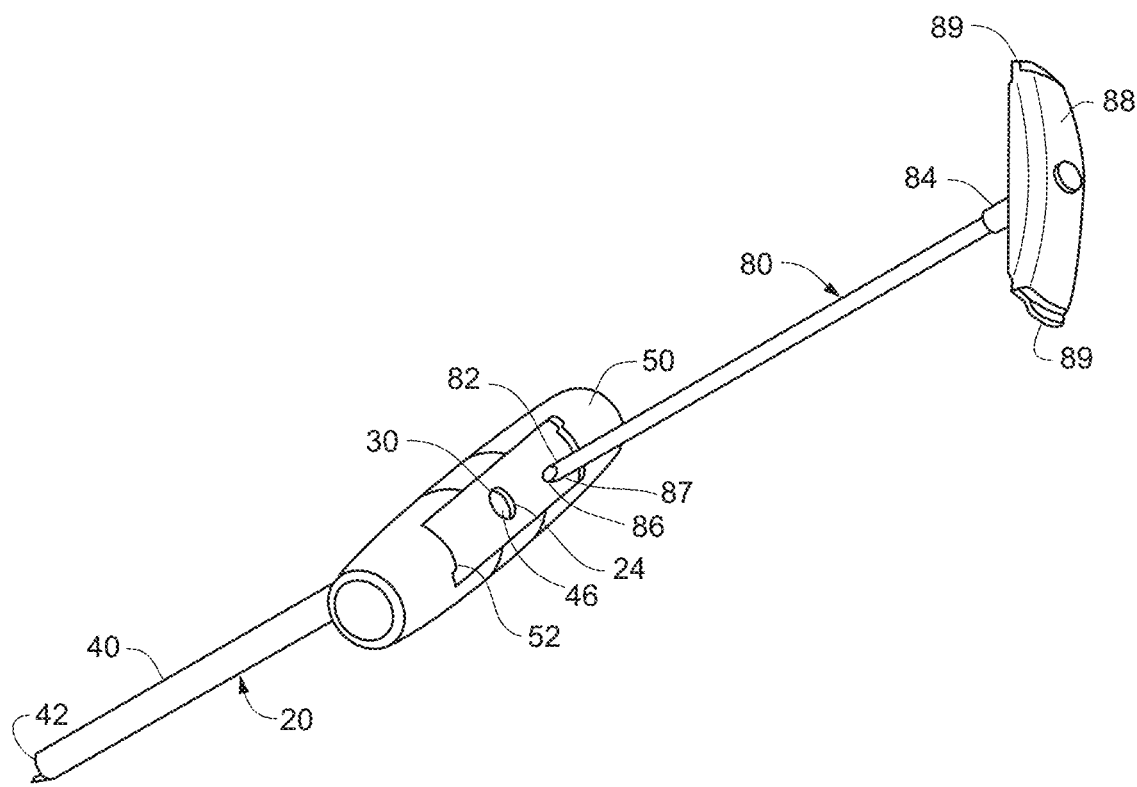
FIG. 3A is an exploded, perspective view of the bone harvester and bone marrow removal system of FIG. 1A including an embodiment of a stylet.
Figure 3B:
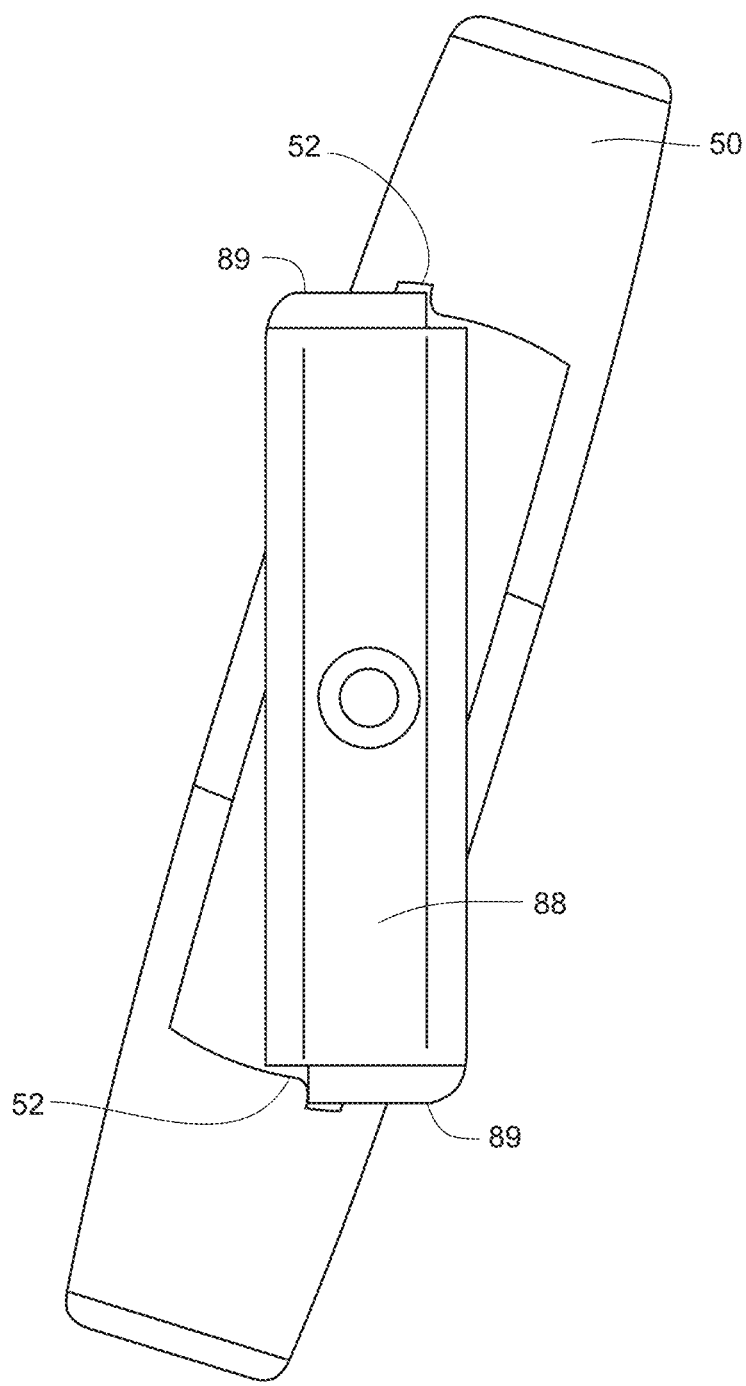
FIG. 3B is a top view of the stylet of FIG. 3A inserted within the bone harvester and bone marrow removal system of FIG. 3A.
Figure 3C:
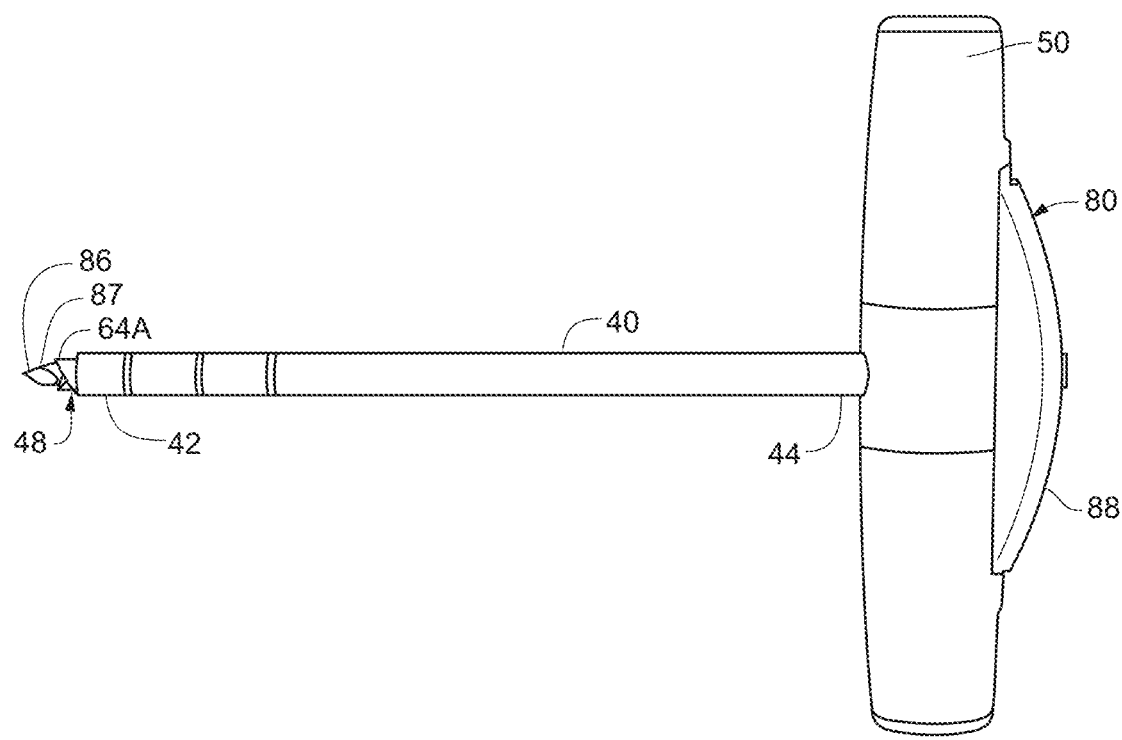
FIG. 3C is a side view of the assembled bone harvester and bone marrow removal system of FIG. 3A including the stylet.
Figure 3D:
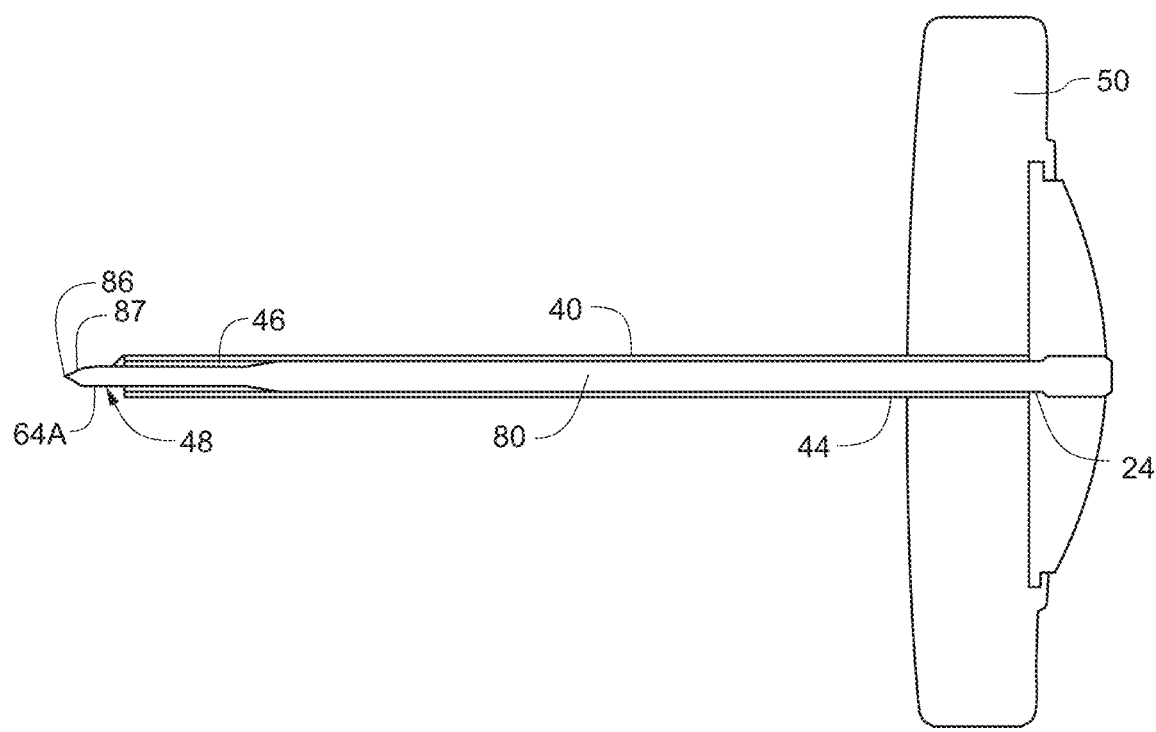
FIG. 3D is a cross-sectional view of FIG. 3C showing the assembled bone harvester and bone marrow removal system of FIG. 3A including the stylet.

In some applications it may be desirable to use one or more additional components to aid in cutting bone and/or drawing a bone marrow sample. FIGS. 3A-3D show an embodiment of the bone harvester and bone marrow removal system 10 including an embodiment of a stylet 80, as an example of one component. FIG. 3A is an exploded, perspective view of the system 10 including an embodiment of the stylet 80. FIG. 3B is a plan view of the stylet 80 inserted within the system 10. FIG. 3C is side view of the assembled system 10 to include the stylet 80. FIG. 3D is a cross-sectional view of FIG. 3C showing the assembled system 10 including the stylet 80.

The stylet 80 has a distal end 82 and a proximal end 84. The distal end 82 can include a pointed tip 86 and at least one cutting edge 87, while the proximal end 84 can include a securing surface 88. The pointed tip can include a triangular shape useful for initially piercing the bone and cutting the bone with the at least one cutting edge as the pointed tip is rotated. The stylet 80 can be adapted to be inserted within the body 40. For example, the stylet 80 can be disposed at least partially within the channel 46, such as by first inserting the distal end 82 through the port 24 and further inserting the stylet 80 within the channel 46 through the port 24 until the securing surface 88 at the proximal end 84 contacts the driver 50. As shown in FIG. 3B, the securing surface 88 can be locked in place at the driver 50, and thus secured to the proximal portion 44 of body 40, such as by rotating the securing surface 88 in a first direction so as to create an interference fit with the locking features 52 at the driver 50. The securing surface 88 may include locking features 89 adapted to mate with the locking features 52 of the driver 50 and create the interference fit in the first direction of rotation of the securing surface 88. In another example, the proximal end 84 may include threads for engaging corresponding threads of the port 24 for securing the stylet 80 to the body 40. In this manner, the proximal end 84 of the style 80 is similarly secured to the proximal portion 44 of the body 40. In addition, various other configurations are also possible for securing the stylet 80 to the body 40.

As shown in FIGS. 3C and 3D, with FIG. 3D being a cross-section of FIG. 3C, the stylet 80 can be received within and secured to the body 40 (e.g., via the port 24), such as at the proximal portion 44 via the driver 50. In the illustrated embodiment, the stylet 80 is dimensioned such that when the stylet 80 is secured to the body 40, and thus a portion of the stylet 80 is within the channel 46, the pointed tip 86 of the stylet 80 extends out from the body 40 (and thus extends out from the channel 46 defined by the body 40). In particular, a distal end of the pointed tip 86 of the stylet 80 can be configured to extend out from the distal portion 42 of the body 40 beyond the apex 64A of the blade of the cutting tip 48. Such a configuration allows the pointed tip 86 of the stylet 80 to be the first point of contact with bone when the system 10 is positioned at an incision. Further, in some embodiments, the stylet can be received within depression sections 74A, 74B of each respective blade 60A, 60B (such sections being shown in FIGS. 2A and D). In such embodiments, the stylet can be generally cylindrical, and a surface of the cylinder can contact sections 74A and 74B for stabilization of the stylet near its distal end 82 during piercing and cutting of bone.

It may be useful to incorporate the stylet 80 in applications of the system 10 for a variety of reasons. For example, the stylet 80 may be utilized in the system 10 during a portion of a procedure, such as during an initial insertion of the system 10 at an incision and prior to a bone marrow sample drawing portion of a procedure. In such an example, the pointed tip 86 can be used to make an initial piercing through bone, optionally rotated to cut bone, and after the stylet 80 has been advanced into the bone to a desired depth the stylet 80 may be unsecured from the body 40 and removed from the body 40 so as to open the channel 46 to allow portions of bone and/or bone marrow to pass into the channel 46. In another example, the pointed tip 86 of the stylet 80 can work in conjunction with the cutting tip 48 of the body 40 to anchor the system 10 at the desired location at the incision and resist undesired sliding movement of the system 10 with respect to the bone. Once the cutting tip 48 has begun to cut bone, and the system 10 is stabilized with respect to the bone, the stylet 80 can be unsecured from the body 40 and removed from the body 40 such that the channel 46 is open and able to receive portions of bone and/or bone marrow.

Figure 4A:
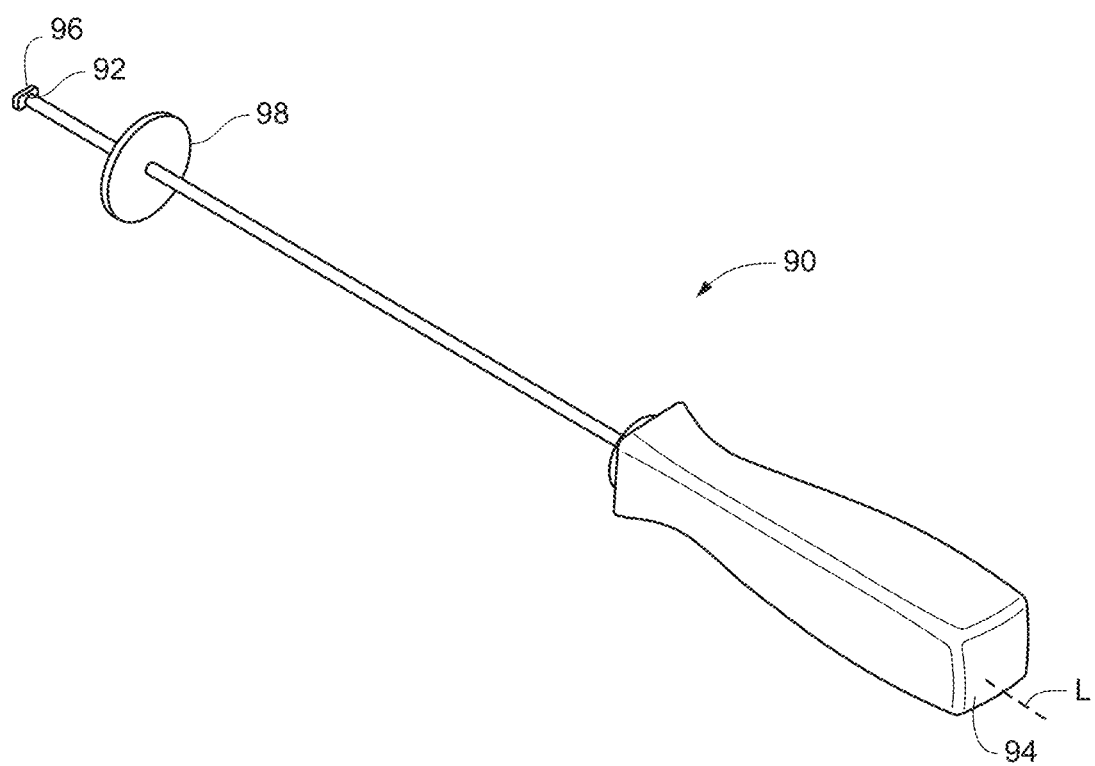
FIG. 4A is a perspective view of an embodiment of a sample removal device.

In addition to the stylet 80, the system 10 can be adapted to receive various other components. FIG. 4A shows a perspective view of an embodiment of a sample removal device 90. As described previously, the bone harvester and bone marrow removal system can cut bone and guide the morselized bone within the channel of the body of the system. The sample removal device 90 may be useful for removing a sample, such as a bone sample, from within the body (e.g., retained in the channel).

In the example shown in FIG. 4A, the device 90 has a distal end 92, a proximal end 94, and a longitudinal axis L extending from the distal end 92 to the proximal end 94. The distal end 92 of the device 90 can include, in some embodiments, a contact surface 96 configured to engage with a sample and push it out from the body of the system. The contact surface 96 can also be configured to avoid interference with the cutting tip of the body of the system. For example, the contact surface 96 may extend substantially perpendicular to the longitudinal axis L of the device 90. Thus, when the apex of one or more blades at the distal portion of the body extend radially inward over a portion of the channel, the contact surface 96 can still be inserted within the channel without interference from the one or more blades. Yet, the perpendicular configuration of the contact surface 96 still allows the contact surface 96 to contact substantially all of the sample along a width of the channel of the body so as to efficiently remove the sample. The proximal end 94 of the device 90 can include a handle as shown. The device 90 is also shown to include a disc 98 on the device 90. The disc 98 can be slidingly retained along the device 90, such as along a shaft of the device 90, allowing the disc 98 to be advanced along the device 90 during a sample removal procedure.

Figure 4B:
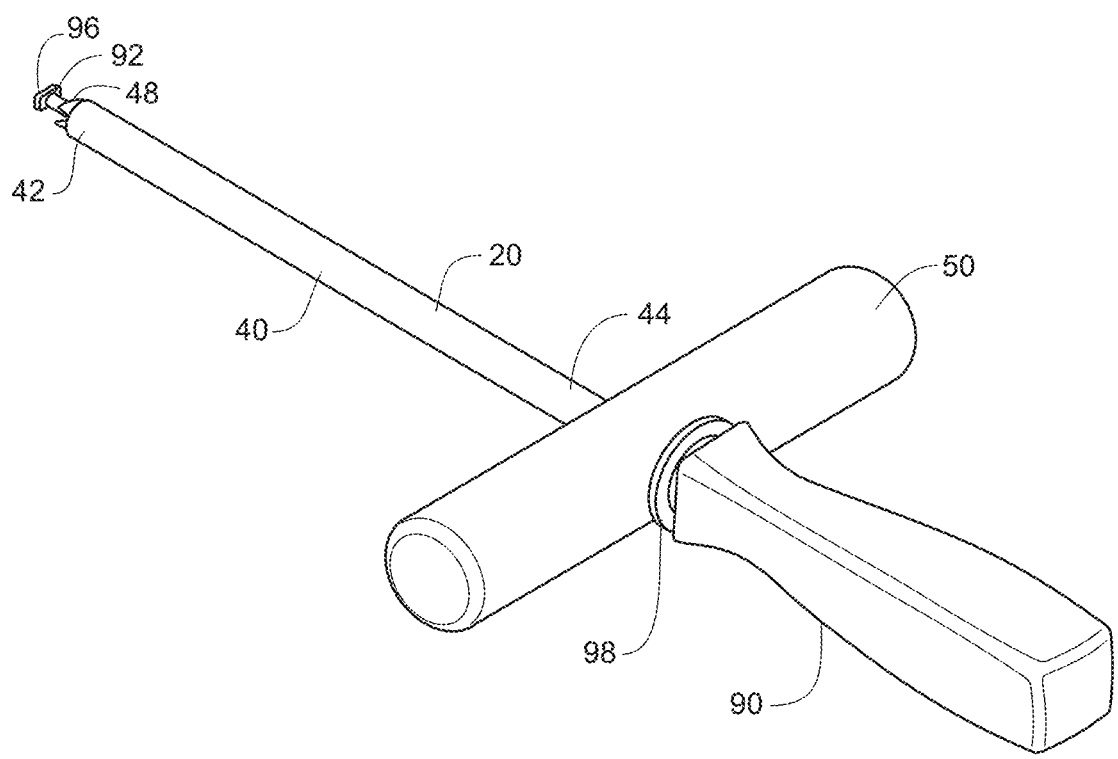
FIG. 4B is a perspective view of the sample removal device of FIG. 4A inserted into an embodiment of a bone harvester and bone marrow removal system from a first direction.
Figure 4C:
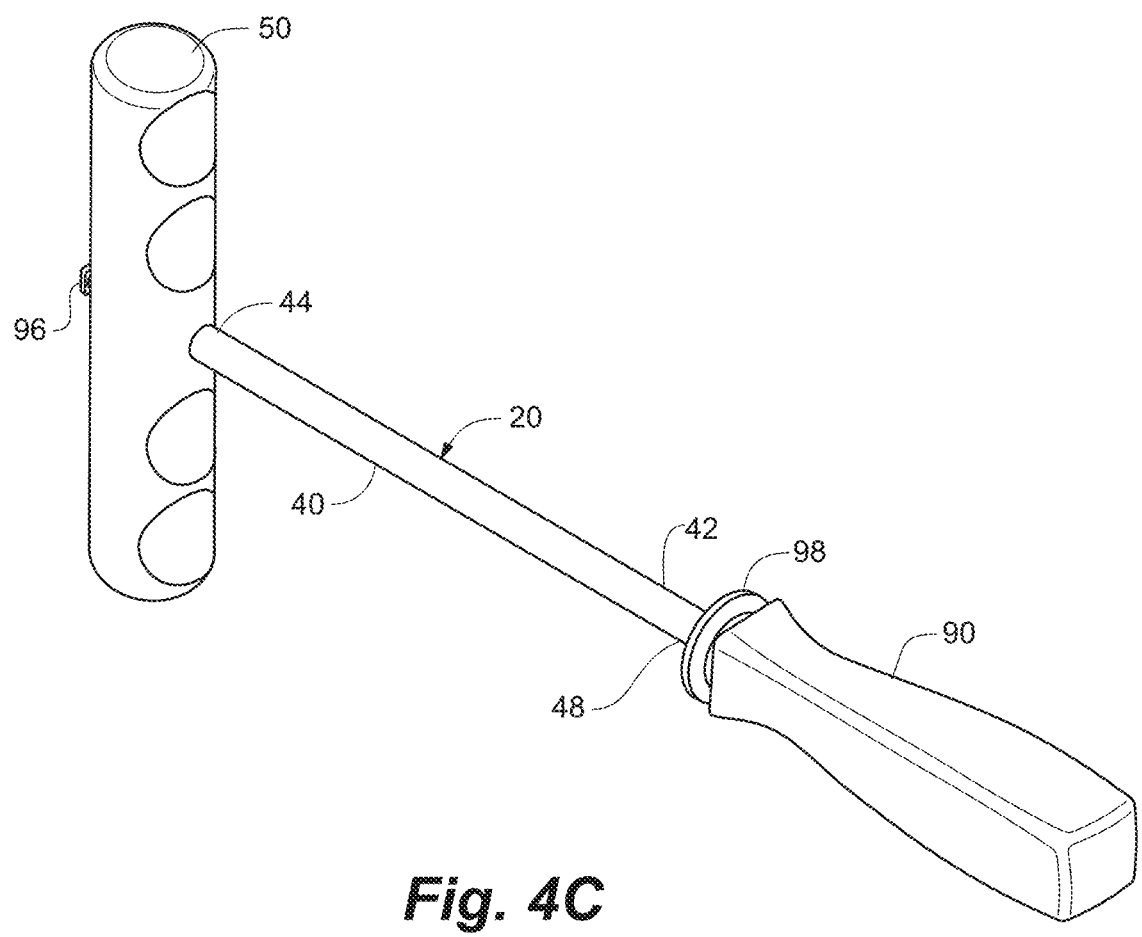
FIG. 4C is a perspective view of the sample removal device of FIG. 4A inserted into an embodiment of a bone harvester and bone marrow removal system from a second direction.

FIGS. 4B and 4C show perspective views of the sample removal device 90 inserted into the bone harvester and bone marrow removal system 10 from opposite ends of the system 10. FIG. 4B shows the device 90 inserted at a proximal portion 44 of the body 40. In one application, the device 90 can be inserted at the proximal portion 44 through the bone marrow sample connector at the driver 50 and into the channel defined by the body 40. The device 90 may be dimensioned so as to have a length that allows the distal end 92 of the device 90 to extend out from the distal portion 42 of the body 40 when the device 90 is inserted within the body 40. As such, a sample retained within the channel of the body 40 will be pushed through the channel as the device 90 is continually advanced through the body 40 from the proximal portion 44 to the distal portion 42. The sample can thus be pushed out from the body 40 at the distal portion 42 through the cutting tip 48. As noted previously, the contact surface 96 on the distal end 92 allows the distal end 92 to avoid interference with the blades at the cutting tip 48 so as to allow substantially all of the sample retained within the body 40 to be pushed out.

FIG. 4C shows the device 90 inserted at a distal portion 42 of the body 40. In one application, the device 90 can be inserted at the distal portion 42 of the body 40 through the cutting tip 48 as is shown. As described previously, the contact surface 96 may be configured to avoid interference with the blades at the cutting tip 48. The contact surface 96 can be advanced within the body 40 to push the sample retained within the body 40 (e.g., within the channel) from the distal portion 42 out the proximal portion 44, such as at the bone marrow sample connector. The disc 98 can slide along the device 90 as the device 90 is advanced within the body 40, and may reduce undesired contact with the cutting tip 48 when the device 90 is inserted through the distal region 42 as shown in FIG. 4C.

Figure 4D:
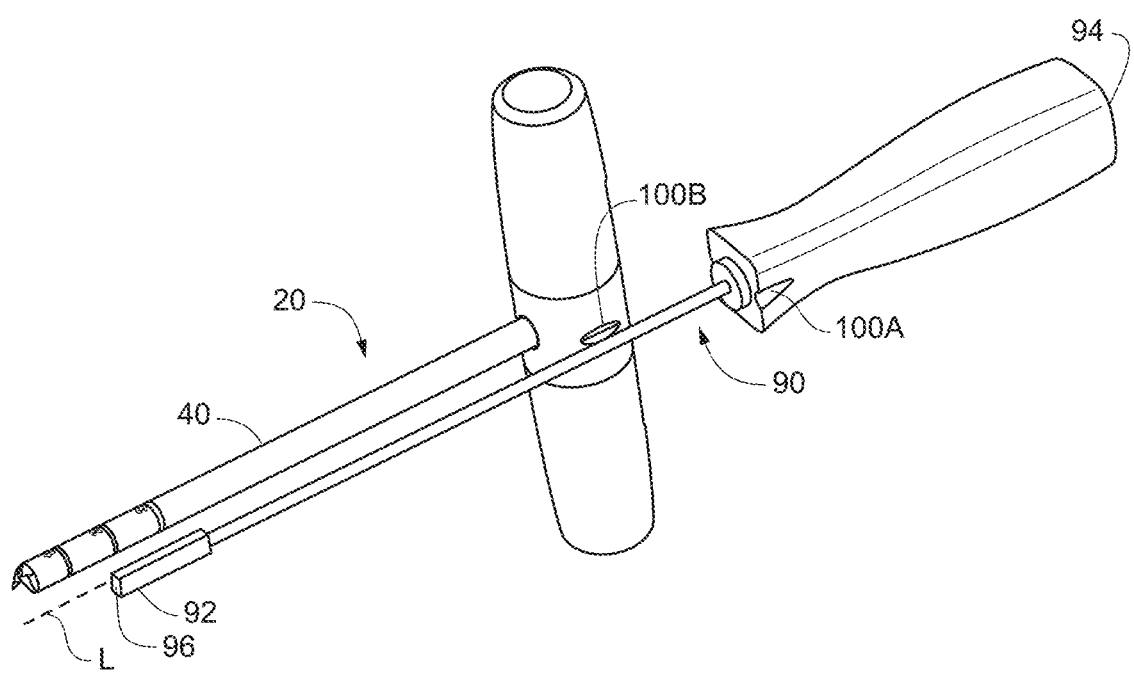
FIG. 4D is a perspective view of a second embodiment of a sample removal device and an embodiment of a bone harvester and bone marrow removal system.

FIG. 4D shows a perspective view of a second embodiment of a sample removal device 90, which can also be used to remove a retained sample from a body 40 of a bone harvester 20, as described with respect to the embodiment shown in FIGS. 4A-C. In the example shown in FIG. 4D, the device 90 has a distal end 92, a proximal end 94, and a longitudinal axis L extending from the distal end 92 to the proximal end 94.

As shown, the distal end 92 of the device 90 can include a contact surface 96 configured to engage with a sample and push it out from the bone harvester body 40. The contact surface 96 can also be configured to avoid interference with a cutting tip of the bone harvester. For example, the contact surface 96 may extend substantially perpendicular to the longitudinal axis L of the device 90. Thus, when the apex of one or more blades at the distal portion of the body extend radially inward over a portion of the channel, the contact surface 96 can still be inserted within the channel without interference from the one or more blades. Yet, the perpendicular configuration of the contact surface 96 still allows the contact surface 96 to contact substantially all of the sample along a width of the channel of the body so as to efficiently remove the sample. The proximal end 94 of the device 90 can include a handle as shown.

Figure 4E:
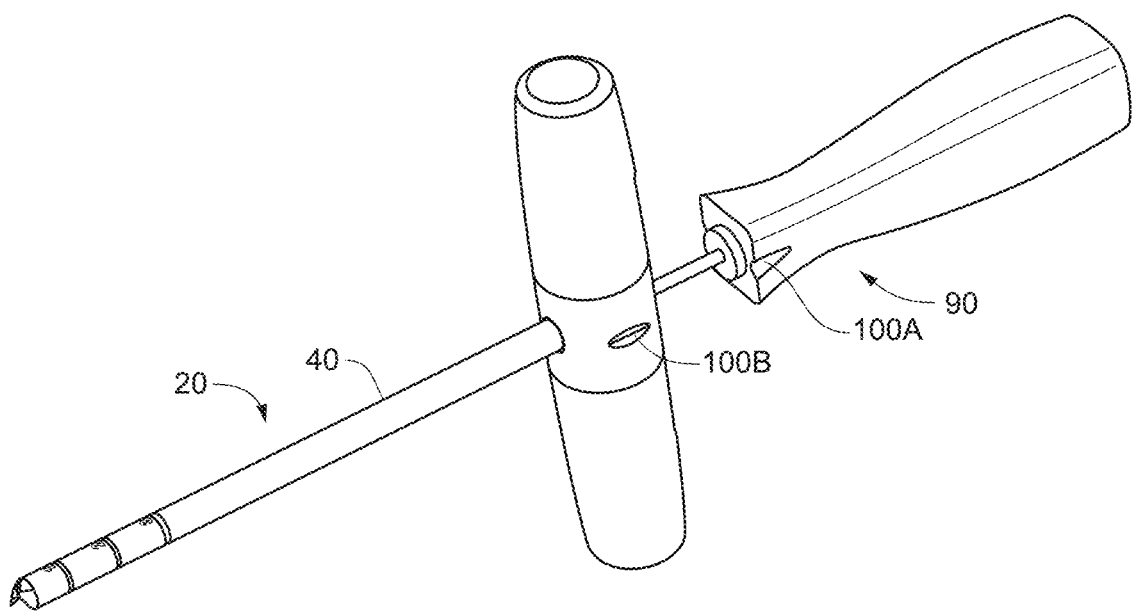
FIG. 4E is a perspective view of the sample removal device of FIG. 4D partially inserted into the bone harvester and bone marrow removal system of FIG. 4D.
Figure 4F:
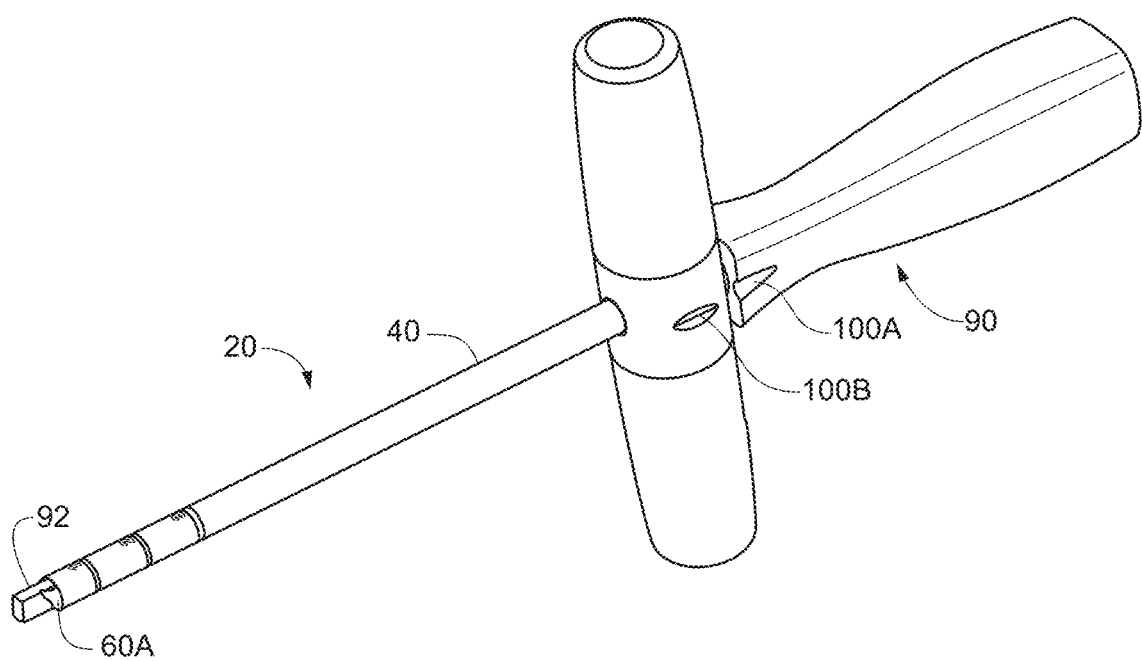
FIG. 4F is a perspective view of the sample removal device of FIG. 4D fully inserted into the bone harvester and bone marrow removal system of FIG. 4D.

As shown, corresponding radial alignment indicators (e.g., notches) 100A, 100B can be provided on the device 90 and bone harvester 20. Such indicators provide a visual guide to the user to facilitate radial alignment of the device 90 with respect to the bone harvester 20 during use to reduce interference between the contact surface 96 and blades of the bone harvester. FIG. 4E depicts the device 90 partially inserted into the bone harvester 20, while FIG. 4F depicts the device 90 fully inserted into the bone harvester 20, with the radial alignment indicators 100A, 100B aligned. As shown in FIG. 4F, when the radial alignment indicators 100A, 100B are aligned and the device 90 is fully inserted, a portion of the distal end 92 extends out of the channel of the bone harvester body 40 and is radially aligned with respect to the body 40 to avoid interference with blades 60A or 60B (60B not shown in FIG. 4F).

Figure 4G:
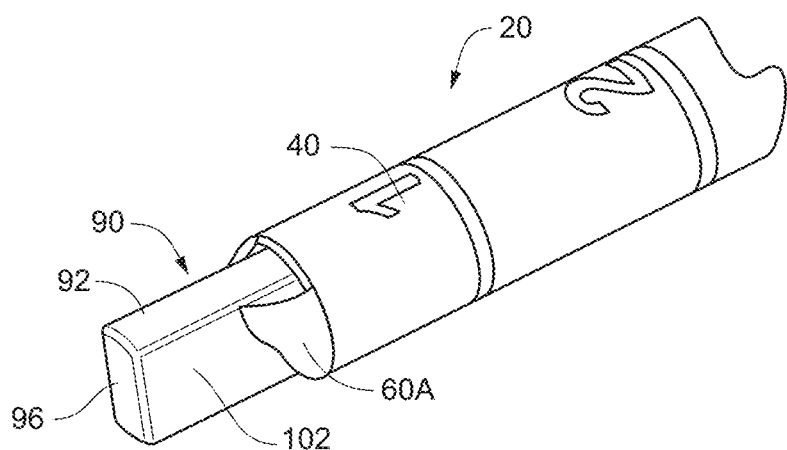
FIG. 4G is a perspective view of a tip of the sample removal device of FIG. 4D fully inserted into the bone harvester and bone marrow removal system of FIG. 4D.
Figure 4H:
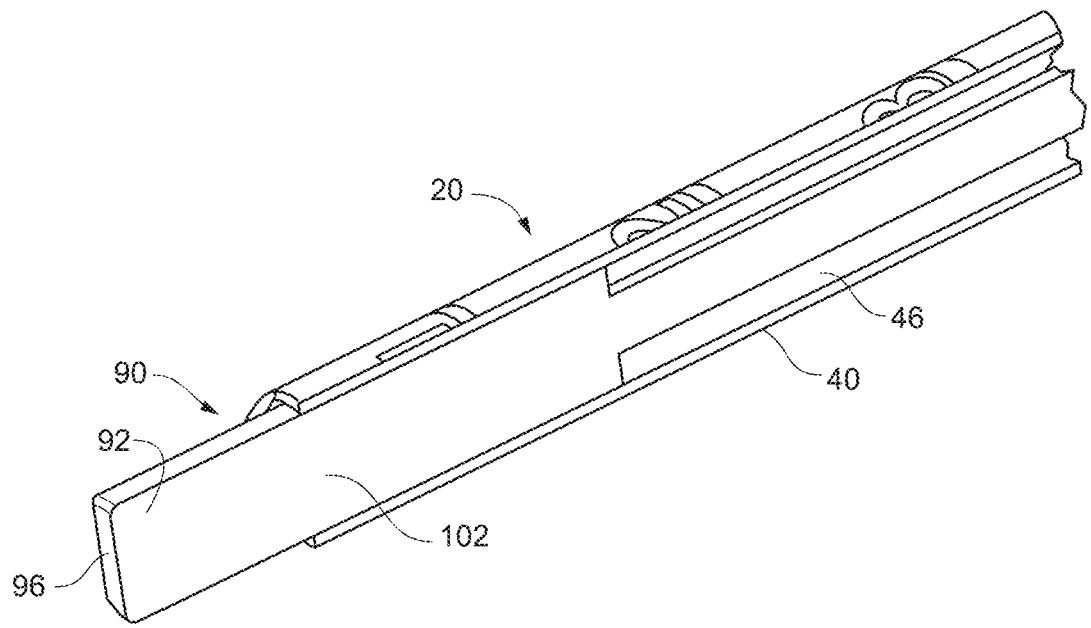
FIG. 4H is a perspective cross-sectional view of the sample removal device of FIG. 4D fully inserted into the bone harvester and bone marrow removal system of FIG. 4D.

FIGS. 4G and 4H show a perspective view and a perspective cross-sectional view, respectively, of the distal end 92 of the device 90 fully inserted into a bone harvester 20. In the embodiment shown, the leading contact surface 96 is part of a paddle 102 on the distal end 92 of the device 90. The paddle 102 has a portion that resides within the channel 46 and a portion that resides distally beyond the bone harvester 20 when the device 90 is fully inserted into the bone harvester. Such a paddle 102 is useful for reducing binding between the device 90 and bone harvester 20 during use.

In an exemplary use of the bone harvester and bone marrow removal system, both a bone sample and a bone marrow sample can be obtained at a single location (e.g., a single incision). In one embodiment, a stylet can be inserted within at least a portion of the channel defined by the body prior to cutting bone at the incision. The stylet can be inserted within the channel such that a pointed tip of the stylet extends out from the channel at the distal portion of the body, allowing the pointed tip of the stylet to be the first point of contact with bone. The stylet can, for example, be used penetrate an outer cortex of a bone. Then, while the pointed tip of the stylet contacts bone, the distal portion of the body, including the cutting tip at the distal portion of the body, can be aligned at the incision.

Bone can then be cut (e.g., morselized) at the first incision, in embodiments with or without the stylet, by causing the bone harvester to be rotationally driven. The bone being cut can be bone material surrounding an initial bone piercing caused by the stylet. The bone can be morselized using the cutting tip at the distal portion of the body, and the morselized bone may be directed into the channel of the body using the blades of the cutting tip. In embodiments where the stylet is inserted into the body, the stylet can be removed once bone has begun to be cut so as to open the channel for receiving the morselized bone. This morselized bone can be continually directed into the channel and retained within the channel during cutting. In some embodiments, the morselized bone retained within the channel can be removed from the body by inserting a sample removal device within the channel. The sample removal device can be used to push the retained bone out from the channel.

In addition, in some examples the bone harvester and bone marrow removal system can also be used to draw a bone marrow sample at the single incision (the same location where the bone is cut). This can be done, in one instance, by advancing the cutting tip of the bone harvester to a desired depth via continual rotation of the body. In one embodiment, the bone marrow sample can be drawn after the morselized bone has been removed from the channel. For example, the bone marrow sample can be drawn from a bone marrow sample connector in fluid communication with the channel of the body. The bone marrow sample may be, in one embodiment, on a proximal portion of the body opposite the cutting tip. The bone marrow sample can be drawn, for instance, by connecting a suction device to the bone marrow sample connector such that the suction device is in fluid communication with the channel of the body allowing the bone marrow sample to be passed through at least a portion of the channel using the suction device.

In a further embodiment, the morselized bone and the bone marrow sample from the incision can be mixed (e.g., to form a bone matrix compound) and introduced at a location spaced from the incision. For example, some such embodiments can include cutting bone at the location spaced from the incision using the bone harvester or any other suitable cutting device, and injecting the morselized bone and bone marrow mixture at the cut location spaced from the incision. Once the mixture has been introduced at the cut location spaced from the incision, a bone plate can be fixed at or near the location spaced from the incision where the bone is cut.

Figure 5:
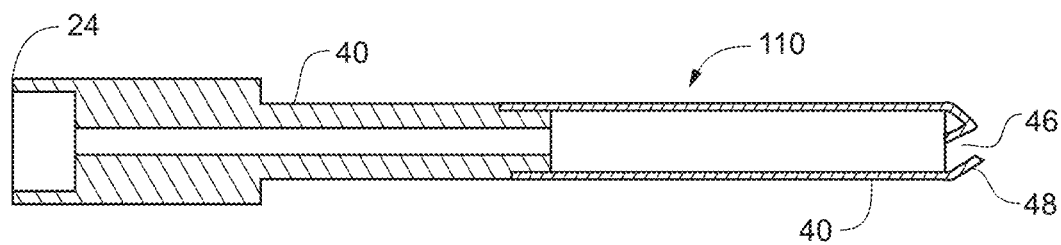
FIG. 5 is a cross-sectional view of another embodiment of a bone harvester device.

FIG. 5 illustrates a cross-section view of another embodiment of a bone harvester device 110. The bone harvester device 110 can have similar features as those described previously, except that the bone harvester device 110 does not have a bone marrow sample connector. As such, the device 110 can be used to cut bone similar to the manner described previously such that bone is morselized by the cutting tip 48 and morselized bone is directed into the interior channel 46 of the body 40. The bone retained within the channel 46 can similarly be removed using a sample removal device.

Figure 6A:
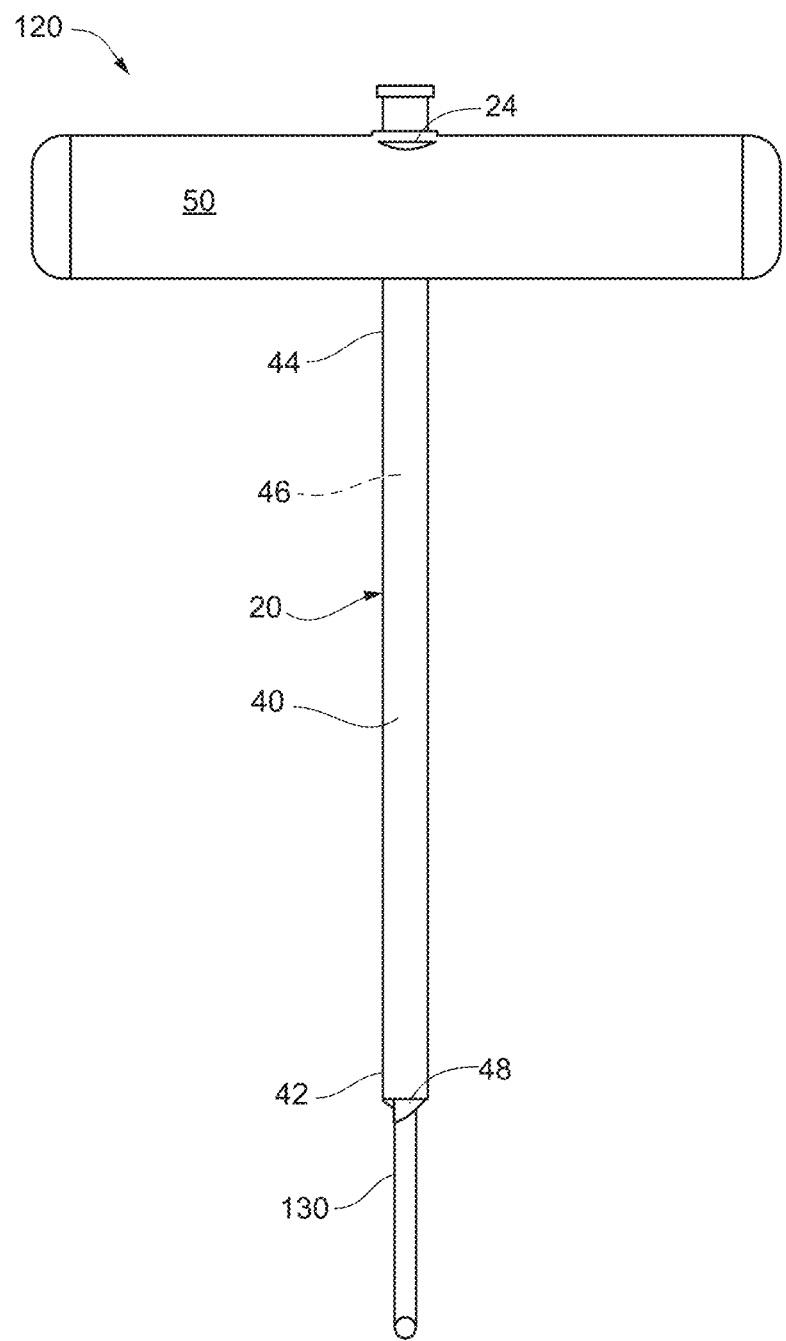
FIG. 6A is a plan view of an embodiment of a bone harvester with an integrated bone marrow needle.
Figure 6B:
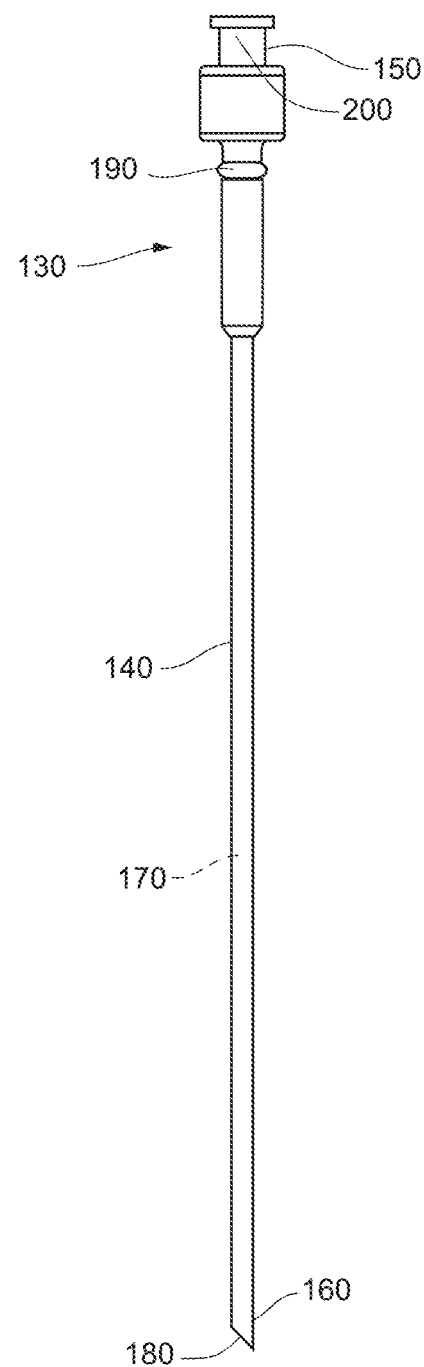
FIG. 6B is a plan view of an embodiment of the bone marrow needle included in the bone harvester of FIG. 6A

FIGS. 6A-6B illustrate another embodiment of a bone harvester device 120. FIG. 6A shows a plan view of the bone harvester 120 including a bone marrow needle 130 disposed within a channel of the body, and FIG. 6B shows a plan view of the bone marrow needle 130 in isolation. The bone harvester 120 can have similar features to those described previously. The bone harvester 120 can draw bone marrow from the same location (e.g., incision) where bone is cut using the bone harvester 120 by using the bone marrow needle 130.

The bone marrow needle 130 can be disposed partially within the channel 46 defined by the body 40. The bone marrow needle 130 can have a body 140 with a proximal end 150 and a distal end 160. The body 140 can define a lumen 170 extending longitudinally within the body 140 from the proximal end 150 to the distal end 160. The distal end 160 of the needle 130 can include a cutting edge 180. The needle 130 can be dimensioned relative to the body 40, of the bone harvester 20, such that the cutting edge 180 on the distal end 160 extends out from the distal portion 42 of the body 40.

In addition, the needle 130 can include a connector 190 for securing the needle 130 to the body 40, such as at the proximal portion 44, and in some examples at the driver 50. In some embodiments, the connector 170 is a compression fit connector in the proximal portion 44 of the body 40. In certain embodiments, the connector 170 includes a compressible O-ring positioned about an exterior surface of the needle and in apposition to an aperture defined by the driver 50. The channel 46 defined by the body 40 can also facilitate centering and stabilization of the needle 130. The needle 130 can also include a connector 200 for coupling to an external device or a stylet similar to that described previously. Thus, where the needle 130 and the stylet are used with the bone harvester, the stylet can be disposed within the lumen 170 of the needle 130, and the needle 130 can be disposed within the channel 46 of the body 40. Furthermore, the stylet may be removed from the lumen 170 independent of the needle 130. The stylet, needle 130, and body 40 can be dimensioned such that the distal end of the stylet extends out from the distal end 160 of the needle 130, and the distal end 160 of the needle 130 extends out from the distal portion 42 of the body 40.

Embodiments of the invention also include a disposable, sterile kit that includes an embodiment of a bone harvester described herein. Other components that may be included within the sterile kit include a suction device, a stylet, a sample removal device, and/or a bone marrow needle.

In use, the needle 130 can be used to draw a bone marrow sample from the incision where bone is cut, while the needle 130 is within the body 40. The bone marrow sample can be drawn at the cutting edge 180 up into the lumen 170 where the sample can be retained.

Thus, embodiments of the invention are disclosed. Although the present invention has been described with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention.

The invention claimed is:

1. A method for obtaining bone and bone marrow, the method comprising:
   rotationally driving a cutting tip at a distal portion of a bone harvester into a bone, thereby morselizing a portion of the bone and causing the morselized bone to enter a channel extending longitudinally through a body of the bone harvester, the channel extending from the distal portion to a proximal portion of the bone harvester; and
   subsequent to morselizing the portion of the bone and causing the morselized bone to enter the channel, drawing bone marrow through the channel,
   wherein rotationally driving the cutting tip into the bone and drawing bone marrow through the channel comprises inserting the bone harvester through an incision and rotationally driving the cutting tip into the bone and drawing bone marrow through the channel while the bone harvester is inserted through the incision.

2. The method of claim 1, wherein the cutting tip includes a first blade comprising,
   a base on a first end of the first blade disposed at the distal portion of the body, wherein the base extends along the distal portion of the body defining the channel from a first edge of the base to a second edge of the base, and
   an apex on a second end of the first blade substantially opposite the first end in a direction spaced from the distal portion of the body, wherein the apex extends radially out relative to the distal portion of the body defining the channel over at least a portion of the channel.

3. The method of claim 1, further comprising:
   inserting a stylet within at least a portion of the channel prior to morselizing bone, the stylet having a distal end and a proximal end, wherein a cutting edge is included on the distal end, and wherein the stylet is inserted within the channel such that the cutting edge extends out from the channel at the distal portion of the body, and
   contacting the bone with the cutting edge of the stylet prior to rotationally driving the cutting tip of the bone harvester against the bone.

4. The method of claim 3, further comprising:
   removing the stylet from the channel after the bone harvester has begun to be rotationally driven such that the morselized bone can pass into the channel at the distal portion of the body.

5. The method of claim 1, further comprising:
   retaining morselized bone within the channel while rotationally driving the cutting tip; and
   removing morselized bone from the channel by inserting a sample removal device within the channel.

6. The method of claim 1, wherein drawing bone marrow though the channel comprises:
   connecting a suction device to a bone marrow sample connector on the bone harvester such that the suction device is in fluid communication with the channel and drawing fluid directly through the channel.

7. The method of claim 1, wherein drawing bone marrow through the channel comprises:
   connecting a suction device to a bone marrow needle disposed in the channel and drawing fluid through the bone marrow needle.

8. The method of claim 1, further comprising: cutting bone at a location spaced from the incision; and introducing a mixture of the morselized bone and the drawn bone marrow from the incision at or near the location where the bone is cut.

9. The method of 1, further comprising removing morselized bone from the channel prior to drawing bone marrow through the channel.

10. The method of claim 1, wherein drawing bone marrow through the channel comprises drawing bone marrow through the channel with the morselized bone in the channel, thereby providing a mixture of morselized bone and bone marrow.

11. The method of claim 1, wherein rotationally driving the cutting tip of the bone harvester comprises rotationally driving the cutting tip with hand power.

12. The method of claim 1, wherein rotationally driving the cutting tip of the bone harvester comprises rotationally driving the cutting tip with a mechanical driving device.

13. The method of claim 1, wherein rotationally driving the cutting tip of the bone harvester comprises rotationally driving the cutting tip in oscillating rotational directions.

14. The method of claim 1, wherein rotationally driving the cutting tip of the bone harvester comprises rotationally driving the cutting tip in a unidirectional direction.

15. The method of claim 1, wherein the bone harvester comprises a connector at the proximal portion, and further comprising, after rotationally driving the cutting tip but prior to drawing bone marrow through the channel, attaching a vacuum source to the bone harvester at the connector.

* * * * *

UNITED STATES PATENT AND TRADEMARK OFFICE
CERTIFICATE OF CORRECTION

| | |
|---|---|
| PATENT NO. | : 11,020,244 B2 |
| APPLICATION NO. | : 15/894686 |
| DATED | : June 1, 2021 |
| INVENTOR(S) | : F. Barry Bays et al. |

It is certified that error appears in the above-identified patent and that said Letters Patent is hereby corrected as shown below:

In the Claims

In Column 14, Line 28, Claim 9, delete "1," and insert -- claim 1, --

Signed and Sealed this
Eighteenth Day of January, 2022

Drew Hirshfeld
*Performing the Functions and Duties of the
Under Secretary of Commerce for Intellectual Property and
Director of the United States Patent and Trademark Office*